US011944462B2

(12) United States Patent
Lin et al.

(10) Patent No.: US 11,944,462 B2
(45) Date of Patent: Apr. 2, 2024

(54) HEART RATE MEASUREMENT USING ADAPTIVE HARMONICS FILTERING

(71) Applicant: University of Florida Research Foundation, Inc., Gainesville, FL (US)

(72) Inventors: Jenshan Lin, Gainesville, FL (US); Linda Frances Hayward, Gainesville, FL (US); Tien-yu Haung, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 42 days.

(21) Appl. No.: 17/462,665

(22) Filed: Aug. 31, 2021

(65) Prior Publication Data

US 2021/0393208 A1    Dec. 23, 2021

Related U.S. Application Data

(63) Continuation of application No. 16/093,846, filed on Oct. 15, 2018, now Pat. No. 11,129,576, which is a
(Continued)

(51) Int. Cl.
*A61B 5/024*     (2006.01)
*A61B 5/00*      (2006.01)
(Continued)

(52) U.S. Cl.
CPC ............ *A61B 5/725* (2013.01); *A61B 5/0205* (2013.01); *A61B 5/024* (2013.01); *A61B 5/0816* (2013.01);
(Continued)

(58) Field of Classification Search
CPC ..... A61B 5/024; A61B 5/1135; A61B 5/0816; A61B 5/0205; A61B 5/7246; A61B 5/725;
(Continued)

(56) References Cited

U.S. PATENT DOCUMENTS

| 4,513,748 A | 4/1985 | Nowogrodzki et al. |
| 2005/0128127 A1 | 6/2005 | Tevs et al. |

(Continued)

FOREIGN PATENT DOCUMENTS

| RU | 2345704 C2 | 2/2009 |
| WO | 2009009690 A2 | 1/2009 |
| WO | 2014196864 A1 | 12/2014 |

OTHER PUBLICATIONS

International Search Report for PCT/US2017/027597 dated Jul. 26, 2017.
(Continued)

*Primary Examiner* — Deborah L Malamud
(74) *Attorney, Agent, or Firm* — Thomas | Horstemeyer, LLP

(57) ABSTRACT

Various examples are provided for accurate heart rate measurement. In one example, a method includes determining a respiratory rate (RR) and respiration displacement from radar-measured cardiorespiratory motion data; adjusting notch depths of a harmonics comb notch digital filter (HCNDF) based upon the respiration displacement; generating filtered cardiorespiratory data by filtering the radar-measured cardiorespiratory motion data with the HCNDF; and identifying a heart rate (HR) from the filtered cardiorespiratory data. In another example, a system includes radar circuitry configured to receive a cardiorespiratory motion signal reflected from a monitored subject; and signal processing circuitry configured to determine a respiration displacement based upon the cardiorespiratory motion signal; adjust notch depths of a HCNDF based upon the respiration displacement; filter the cardiorespiratory motion data with the HCNDF; and identifying a heart rate (HR) from the filtered cardiorespiratory data.

21 Claims, 20 Drawing Sheets

Related U.S. Application Data continuation of application No. PCT/US2017/027597, filed on Apr. 14, 2017.

(60) Provisional application No. 62/322,947, filed on Apr. 15, 2016.

(51) Int. Cl.
| | |
|---|---|
| A61B 5/0205 | (2006.01) |
| A61B 5/08 | (2006.01) |
| A61B 5/113 | (2006.01) |
| G01S 7/41 | (2006.01) |
| G01S 13/536 | (2006.01) |
| G01S 13/88 | (2006.01) |

(52) U.S. Cl.
CPC .......... *A61B 5/1135* (2013.01); *A61B 5/4839* (2013.01); *A61B 5/7246* (2013.01); *G01S 7/415* (2013.01); *G01S 13/536* (2013.01); *G01S 13/88* (2013.01)

(58) Field of Classification Search
CPC ....... A61B 5/4839; G01S 13/88; G01S 7/415; G01S 13/536
See application file for complete search history.

(56) References Cited

U.S. PATENT DOCUMENTS

| | | |
|---|---|---|
| 2007/0076782 A1 | 4/2007 | McCorkle et al. |
| 2009/0278728 A1 | 11/2009 | Morgan et al. |
| 2019/0219687 A1 | 7/2019 | Baheti et al. |

OTHER PUBLICATIONS

Li et al. "Harmonics Cancellation in Noncontact Microwave Doppler Radar Cardiopulmonary Sensing". International Journal of Digital Content Technology and its Applications(JDCTA). vol. 6, No. 9 (May 2012) pp. 147-156.

Zhang et al., "The Separation of the Heartbeat and Respiratory Signal of a Doppler radar based on the LMS adaptive harmonic cancellation algorithm" Sixth International Symposium on Computational Intelligence and Design, vol. 1, pp. 362-364 , Oct. 2013.

Droitcour et al., "A Microwave Radio for Doppler Radar Sensing of Vital Signs," Microwave Symposium Digest, 2001 IEEE MTT-S International; vol. 1; pp. 175-178; May 2001.

Lubecke et al., "10 GHZ Doppler Radar Sensing of Respiration and Heart Movement," 2002 Bioengineering Conference, Proceedings of the IEEE 28th Annual Northeast; pp. 55-56; 2002.

Li et al., "Harmonics Cancellation in Noncontact Microwave Doppler Radar Cardiopulmonary Sensing," International Journal of Digital Content Technology and its Applications 6(9):147-156; May 2012.

Huang et al., "Non-Invasive Measurement of Laboratory Rat's Cardiorespiratory Movement Using a 60-GHZ Radar and Nonlinear Doppler Phase Modulation," RF and Wireless Technologies for Biomedical and Healthcare Applications (IMWS-BIO), 2015 IEEE MTT-S 2015 International Microwave Workshop Series; pp. 83-83; Sep. 2015.

FREQUENCY OF DG HARMONICS SATISFIED $x = f_h p + f_r q$ AND ITS AMPLITUDE $H_x$ WITH BESSEL FUNCTION EXPRESSION

|  | $x$ (Hz) | $p$ | $q$ | $|H_x|$ |
|---|---|---|---|---|
| $H_{RR}$ | 0.7 | 0 | 1 | $J_0(a_h)J_1(a_r)$ |
| $H_{2RR}$ | 1.4 | 0 | 2 | $J_0(a_h)J_2(a_r)$ |
| $H_{3RR}$ | 2.1 | 0 | 3 | $J_0(a_h)J_3(a_r)$ |
| $H_{4RR}$ | 2.8 | 0 | 4 | $J_0(a_h)J_4(a_r)$ |
| $H_{HR-4RR}$ | 4.2 | 1 | -4 | $J_1(a_h)J_{-4}(a_r)$ |
| $H_{HR-3RR}$ | 4.9 | 1 | -3 | $J_1(a_h)J_{-3}(a_r)$ |
| $H_{HR-2RR}$ | 5.6 | 1 | -2 | $J_1(a_h)J_{-2}(a_r)$ |
| $H_{HR-RR}$ | 6.3 | 1 | -1 | $J_1(a_h)J_{-1}(a_r)$ |
| $H_{HR}$ | 7 | 1 | 0 | $J_1(a_h)J_0(a_r)$ |
| $H_{HR+RR}$ | 7.7 | 1 | 1 | $J_1(a_h)J_1(a_r)$ |
| $H_{HR+2RR}$ | 8.4 | 1 | 2 | $J_1(a_h)J_2(a_r)$ |
| $H_{HR+3RR}$ | 9.1 | 1 | 3 | $J_1(a_h)J_3(a_r)$ |
| $H_{HR+4RR}$ | 9.8 | 1 | 4 | $J_1(a_h)J_4(a_r)$ |

MEASUREMENT OF A HEALTHY RAT UNDER ANESTHESIA AT 0-15 S

| Experiment #1 | Respiration | Heartbeat |
|---|---|---|
| Measured Rate | 0.66 Hz | 6.73 Hz |
| Calculated Displacement | 1.19 mm | 0.13 mm |

(a)

(b)

(a)

(b)

HEART RATE MEASUREMENT USING ADAPTIVE HARMONICS FILTERING

CROSS REFERENCE TO RELATED APPLICATIONS

This application is a continuation of U.S. non-provisional application having Ser. No. 16/093,846, filed Oct. 15, 2018, which is the 35 U.S.C. § 371 national stage application of PCT Application No. PCT/US2017/027597, filed Apr. 14, 2017, where the PCT application claims priority to, and the benefit of, U.S. provisional application entitled "Accurate Heart Rate Measurement by Radar Using Adaptive Harmonics Filter" having Ser. No. 62/322,947, filed Apr. 15, 2016, all of which are hereby incorporated by reference in their entireties.

BACKGROUND

Assessment of cardiorespiratory function is a fundamental requirement in a laboratory setting for physiological research. The physiological signs associated with pain include fluctuations in respiratory rate (RR), heart rate (HR), blood pressure and body temperature. Monitoring signs of pain in a laboratory setting is critical for both ensuring animal welfare and drug efficacy studies. A major concern for monitoring physiological response lies in the fact that lab animals require surgical implantation and postoperative recovery prior to the major drug test, which yields unintended effects or even death. The current methods of physiological monitoring are often performed with contact sensors, such as electrocardiography (ECG). Developing a non-invasive method for detecting an animal's physiological response to pain would be a vast improvement over current behavioral or invasive methods for monitoring cardiorespiratory function.

SUMMARY

Aspects of the present disclosure are related to heart rate measurement by radar. A harmonics comb notch digital filter (HCNDF) can be used to the heart rate from cardiorespiratory motion data.

In one aspect, among others, a method for heart rate measurement comprises determining a respiratory rate (RR) and respiration displacement from radar-measured cardiorespiratory motion data; adjusting notch depths of a harmonics comb notch digital filter (HCNDF) based upon the respiration displacement; generating filtered cardiorespiratory data by filtering the radar-measured cardiorespiratory motion data with the HCNDF; and identifying a heart rate (HR) from the filtered cardiorespiratory data. A computing device can be used for one or more operation. In one or more aspects, the respiration displacement can be determined from a respiration fundamental frequency and respiration demodulation-generated (DG) harmonics identified from the radar-measured cardiorespiratory motion data. The notch depths can be based upon amplitudes of the respiration fundamental frequency and the respiration DG harmonics. The notch depths can be based upon one or more ratios of the respiration fundamental frequency and the respiration DG harmonics.

In one or more aspects, notch frequencies of the HCNDF can be adjusted based upon the RR. The notch frequencies of the HCNDF can correspond to a fundamental frequency of the RR and harmonics of the fundamental frequency. The HCNDF can comprise notches corresponding to the fundamental frequency of the RR, a second harmonic frequency, and a third harmonic frequency. The HCNDF can further comprise notches corresponding to a fourth harmonic frequency and a fifth harmonic frequency. In one or more aspects, notch widths of the HCNDF can be based upon a length of a time window over which the radar-measured cardiorespiratory motion data was obtained. The notch widths of the HCNDF can be adjusted in response to a change in the length of the time window. The notch widths can be reduced in response to an increase in the length of the time window. In one or more aspects, the radar-measured cardiorespiratory motion data can be obtained using a 60 GHz radar.

In another embodiment, a system comprises radar circuitry configured to transmit a single-tone carrier signal and receive a cardiorespiratory motion signal reflected from a monitored subject; and signal processing circuitry configured to: determine a respiration displacement from cardiorespiratory motion data based upon the cardiorespiratory motion signal; adjust notch depths of a harmonics comb notch digital filter (HCNDF) based upon the respiration displacement; generate filtered cardiorespiratory data by filtering the cardiorespiratory motion data with the HCNDF; and identifying a heart rate (HR) from the filtered cardiorespiratory data. In one or more aspects, the radar circuitry can comprise a Doppler radar transceiver coupled to transmit and receive antennas. A radar transceiver chip can comprise the radar circuitry and patch antennas as the transmit and receive antennas. The radar transceiver chip and the patch antennas can be disposed on a common substrate. The Doppler radar transceiver can operate at 60 GHz. The signal processing circuitry can comprise data acquisition circuitry configured to sample quadrature signals of the cardiorespiratory motion signal and a processor configured to determine the respiration displacement and identify the HR based upon the sampled quadrature signals.

In one or more aspects, the respiration displacement can be determined from a respiration fundamental frequency and respiration demodulation-generated (DG) harmonics identified from the cardiorespiratory motion data. The notch depths can be based upon amplitudes of the respiration fundamental frequency and the respiration DG harmonics. The signal processing circuitry can be configured to adjust notch frequencies of the HCNDF based upon a respiratory rate (RR) determined from the cardiorespiratory motion data. Notch widths of the HCNDF can be based upon a length of a time window over which the cardiorespiratory motion data was determined. The notch widths of the HCNDF can be adjusted in response to a change in the length of the time window.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
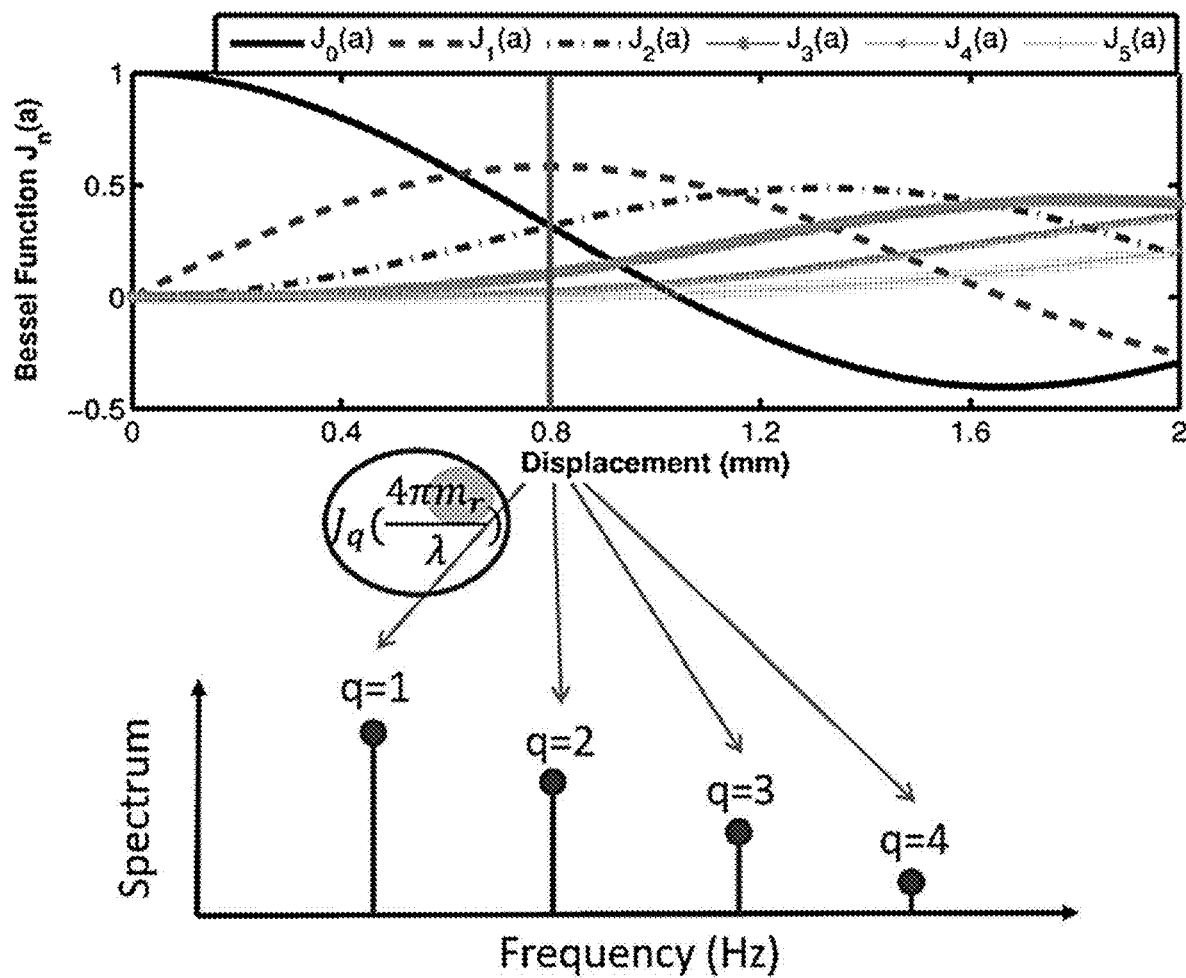
FIG. 1A is an example illustrating the relationship between vibration displacement, Bessel functions, and generated harmonics, in accordance with various embodiments of the present disclosure.

Disclosed herein are various examples of methods and systems related to heart rate measurement by radar. Reference will now be made in detail to the description of the embodiments as illustrated in the drawings, wherein like reference numbers indicate like parts throughout the several views.

When using radar to perform non-contact measurement of vital signs (human or animal), both respiration and heartbeat are detected. The signal of respiration is often much larger than the signal of heartbeat (because of the different body displacements), and the harmonics of the respiration signal (produced by the nonlinear Doppler phase demodulation when the wavelength of radar frequency is approaching the same scale as the respiration displacement) will interfere with the correct reading of the heartbeat signal, which is a much weaker signal. To solve this problem, an adaptive harmonics filter similar to a comb notch filter can be used, but with adaptive attenuation at each harmonic frequency implemented in software (digital domain). The attenuation at each harmonic frequency can be dynamically adjusted based on the signal strength of each harmonic frequency. This way, the right amounts of respiration harmonics can be removed without affecting the heartbeat signal, and the heartbeat signal can be enhanced to provide correct reading of heartbeat rate.

Chest wall movement caused by respiration and heartbeat activities can be quantified with displacement and frequency. Some techniques for measuring displacement of chest wall motion such as impulse cardiogram, capacitance transducer, and magnetic field sensor have been examined. However, they are contact measurements and may affect the measurement accuracy. Laser speckle interferometry does not need body contact, but the surface of the subject has to be smooth and no clothes are allowed. These unintended impacts can be avoided using radar. The development of Doppler radar techniques link biomedical research with noncontact sensing, and brings up various applications. With the goal of developing a non-invasive and non-contact monitoring system for measuring cardiorespiratory movement of a laboratory rat, Doppler radar can be used. Measuring a small animal's vital signs with radar is more challenging than measuring human vital signs due to the smaller chest wall movements. The millimeter-wave Doppler radar can be used for its capability of detecting small movements.

Doppler radar can be used to detect vibration motion and determine both displacement and frequency of the motion. A radar transceiver can transmit an unmodulated signal $T(t) = \cos(2\pi ft + \phi)$ to the rat, where f is the single-tone carrier frequency and $\phi$ is the residual phase, and receives the movements $x(t)$ induced by breathing and heartbeat. The displacement of vibration movements can be extracted from the ratio of measured harmonics in the baseband spectrum. One key advantage is that no calibration is needed when the detection distance changes because the method does not use the absolute power level of each harmonic but the ratio between them. The use of a quadrature system and a complex signal demodulation (CSD) technique can provide the flexibility of selecting harmonic pairs for the ratio. By using multiple harmonic pairs at a fixed carrier frequency, the reliability of measuring the amplitude ratio can be increased. However, monitoring the chest wall movement of small animals by the millimeter-wave radar can cause severe nonlinear effects on the detected baseband spectrum due to the Doppler phase demodulation method. With the capability of measuring both displacement and frequency of motion using radar, a method that utilizes the demodulation-generated harmonics can successfully measure both displacements and frequencies of both respiration and heartbeat movements of the laboratory rat.

Compared to humans, rats have a significantly higher respiratory rate (RR) and heart rate (HR), which are associated with smaller chest-wall movements. The respiration and heartbeat displacements of an adult rat is estimated to be less than 2 mm. A radar operating frequency as high as 60 GHz can be used to detect the small chest-wall movements. Since the wavelength at 60 GHz is 5 mm, and the movement amplitude that can be accurately measured is estimated to be as small as 0.2 mm.

The method is based on the nonlinear Doppler phase demodulation that analyzes the demodulation-generated harmonics and extracted displacements from the harmonic ratios. It can be a potential cardiorespiratory function monitor without electrode or catheter surgical implantation in rats. An adaptive harmonics comb notch digital filter (HCNDF) for removing respiration harmonics is disclosed. Several details will be discussed in the present disclosure. First, how to identify the heart rate (HR) peak on the spectrum. Second, how to properly choose the demodulation-generated harmonics for calculating respiration and heartbeat displacement. Third, if the respiration and heartbeat itself already contain harmonics, the influence of those vibration-generated harmonics on displacement acquisition method should be considered. Fourth, the detection of vibration displacement can be determined by the carrier frequency, and knowing the detection range is beneficial. Finally, measurements were conducted using two different drugs and monitoring the cardiorespiratory response to the delivered drugs over time.

A cardiorespiratory motion comprises respiration and heartbeat, and can be modeled as a two-tone periodic movement x(t), which can be expressed as:

$$x(t) = m_r(2\pi f_r t) + m_h \sin(2\pi f_h t), \quad (1)$$

where $f_r$ is the respiration rate (RR), $f_h$ is the HR, and $m_r$ and $m_h$ are the displacements due to respiration and heartbeat, respectively. When a Doppler radar transmits a single-tone carrier signal toward target, the reflected signal contains the information of the cardiorespiratory motion. By mixing the received signal with part of the transmitted signal as reference, the phase-modulated baseband signal can be expressed as:

$$B(t) = \cos\left[\frac{4\pi x(t)}{\lambda} + \phi\right], \quad (2)$$

where $\lambda$ is the carrier wavelength of radar signal, and $\phi$ is the total residual phase noise. If the displacement m is comparable to the wavelength $\lambda$, the small angle approximation cannot be applied. Since the quadrature (I/Q) radar is used, by applying a complex signal demodulation (CSD) technique, the detected signal can be generated by combining I and Q outputs. However, the nonlinear transfer function produces demodulation-generated (DG) harmonics. As a result, the baseband signal comprises a number of DG harmonics of the fundamental frequency, which can be expressed with a series of the Bessel functions:

$$B(t) = I(t) + jQ(t) = \sum_{p=-\infty}^{\infty} \sum_{q=(x-f_h p)/f_r}^{\infty} J_p(a_h) J_q(a_r) \cdot e^{j2\pi xt} \cdot e^{j\phi}, \quad (3)$$

where J(a) is the first kind Bessel function, $a_r = 4\pi m_r/\lambda$ and $a_h = 4\pi m_h/\lambda$, p and q are integers that satisfy $x = f_h p + f_r q$, and x represents the DG harmonic frequency.

Amplitude of the DG harmonics in the baseband spectrum can be determined by residual phase $\phi$, wavelength $\lambda$, and displacement of vibration m. The term $e^{j\phi}$ can be eliminated since quadrature architecture is used, and the effect of the residual phase on amplitude can be neglected. FIG. 1A illustrates the relationship of the vibration displacement, Bessel functions and the generated harmonics. For a fixed displacement, different orders of Bessel functions correspond to different values, and result in different amplitudes on the detected spectrum. Therefore, for a purely sinusoidal motion, the displacement can be determined from the ratio of the DG harmonics; and for a complex periodic motion, multiple DG harmonic pairs can be used to create more equations to solve the unknown amplitudes of different frequency components.

For the cardiorespiratory motion, the DG harmonics contain frequency components from both RR and HR, and the amplitude $H_x$ can be expressed as:

$$H_x = \left| \sum_{p=-\infty}^{\infty} \sum_{q=(x-f_h p)/f_r}^{\infty} J_p(a_h) J_q(a_r) \right|. \quad (4)$$

Figures 1B, 2:
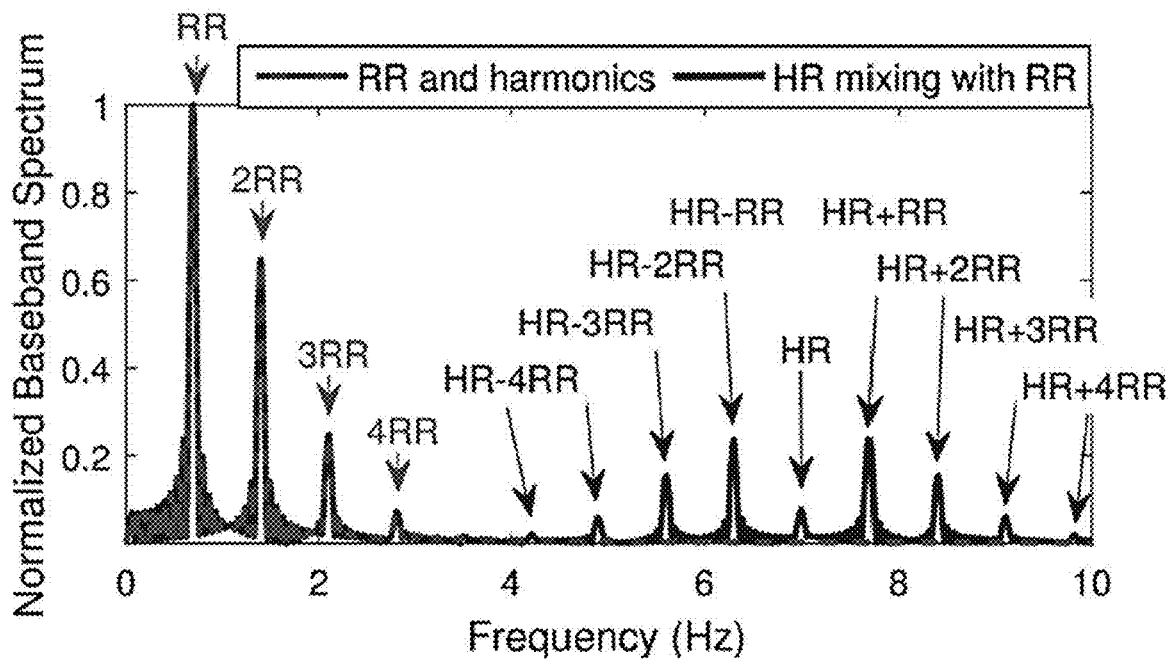
FIG. 1B is an example of a baseband spectrum with identified respiration demodulation-generated (DG) harmonics, in accordance with various embodiments of the present disclosure.
FIG. 2 is a table listing the frequency and amplitude of DG harmonics of the spectrum of FIG. 1, in accordance with various embodiments of the present disclosure.

DG harmonics shown in the baseband spectrum can be grouped into two categories: the respiration and its DG harmonics, and the frequency mixing products of RR and HR. FIG. 1B illustrates an example of the baseband spectrum with identified respiration DG harmonics and mixing products between heart rate (HR) and respiration rate (RR). The mixing products involving higher harmonics of heart rate will fall outside of the baseband of interest and are therefore not considered here. In order to obtain a more accurate DG harmonic ratio that contains the strongest frequency components from the RR, the first selected pair for respiration displacement extraction is the $H_{RR}$ and $H_{2RR}$, and the ratio can be shown as:

$$\frac{H_{RR}}{H_{2RR}} = \frac{|J_0(a_h) J_1(a_r)|}{|J_0(a_h) J_2(a_r)|} = \frac{|J_1(a_r)|}{|J_2(a_r)|}. \quad (5)$$

The two DG harmonics are chosen because they contain the information involving different $J_q(a_r)$ with the same $j_p(a_h)$. Therefore, the same $J_0(a_h)$ can be cancelled out, leaving the $J_q(a_r)$ only for calculating $m_r$. The selection of DG harmonics with x>3RR may be too small to be useful, and the three strongest harmonics are sufficient for displacement extraction and can be expressed as:

$$H_{RR}:H_{2RR}:H_{3RR}=|J_1(a_r)|:|J_2(a_r)|:|J_3(a_r)|. \qquad (6)$$

On the other hand, the heartbeat displacement is extracted by utilizing the stronger mixing products between heart rate and respiration harmonics because the DG harmonics of heart rate are too small. Three mixing products, $H_{HR-RR}$, $H_{HR-2RR}$, and $H_{HR-3RR}$ can be chosen and paired up with the respiration DG harmonics for calculating $m_h$, as shown below:

$$\frac{H_{RR}}{H_{HR-RR}} = \frac{H_{2RR}}{H_{HR-2RR}} = \frac{H_{3RR}}{H_{HR-3RR}} = \frac{|J_0(a_h)|}{|J_1(a_h)|}. \qquad (7)$$

In addition to DG harmonics and vibration-generated (VG) harmonics, another possible source of harmonics is the nonlinearity of the RF and analog circuits in receiver. These harmonics, however, can be controlled and eliminated by keeping signal level small enough to stay within the linear region. In order to take advantage of the nonlinear Doppler phase demodulation effect, it should be noted that the detection accuracy depends on the accuracy of DG harmonic ratio, which means the ratio of m/λ will be important. The larger the ratio, the stronger the nonlinear effect, resulting in more DG harmonics generated on the spectrum. At a fixed wavelength, if the displacement is too small compared to the wavelength, the detection accuracy may be degraded because it might not be able to generate sufficient DG harmonics for obtaining the ratio. In the case of measuring laboratory rat's cardiorespiratory movement, the vibration displacement as well as the radar detection range at carrier wavelength will be discussed.

Heart Rate Identification. As mentioned above, DG harmonics shown on the spectrum can be classified as respiration DG harmonics and HR-mixing products. The amplitude of respiration DG harmonics consist of the same $J_0(a_h)$ and $q^{th}$-order Bessel functions $J_q(a_r)$. In other words, amplitudes of these DG harmonics will be determined by the $J_0(a_h)J_q(a_r)$. On the other hand, it can also be observed from FIG. 1B that the HR mixes with respiration DG harmonics, resulting in these mixing products in the spectrum. These frequency mixing products share the same $J_1(a_h)$ with different order of $J_q(a_r)$, and are symmetrically centered around the HR peak. The symmetry of mixing products is based on $J_q(a_r)$, which means the amplitudes of these mixing products should maintain the same ratio as respiration and its DG harmonics, thus the HR identification possible.

In the example of FIG. 1B, the simulated cardiorespiratory motion is:

$$x(t) = 0.9 \cdot \sin(2\pi \cdot 0.7 \cdot t) + 0.2 \cdot \sin(2\pi \cdot 0.7 \cdot t), \qquad (8)$$

where $m_r$=0.9 mm, $m_h$=0.2 mm, $f_r$=0.7 Hz, and $f_h$=7 Hz are assumed with small animal's vibration pattern. Based on equation (4), the frequency and amplitude of DG harmonics shown on the spectrum are listed in the table of FIG. 2.

Since $J_{-n}(a)$ equals $-J_n(a)$ or $J_n(a)$ for odd or even n, respectively, the amplitude of HR-mixing products for those who share the same $J_n(a)$ should be equal. In other words, the ratios between respiration and its DG harmonics should remain the same when they mix with HR. For example, $H_{HR+RR}$ equals to $H_{HR-RR}$ after taking the absolute value, and the ratios of $H_{RR}/H_{2RR}$ and $H_{HR-RR}/H_{HR-2RR}$ are the same. Therefore, the HR can be identified by knowing the respiration DG harmonics and their ratios. As a result, by categorizing DG harmonics contributed from respiration and heartbeat movements, the HR peak is revealed.

Vibration-Generated Harmonics. The aforementioned analyses are based on the assumption that the cardiorespiratory movement contains respiration and heartbeat which are sinusoidal vibrations. However, it is possible that the respiration or heartbeat movement itself already contains harmonics. The VG harmonics shape the original respiration and heartbeat signal into non-sinusoidal vibrations. The odd-order VG harmonics will distort the waveform more obviously, and create larger deviation in the amplitude ratio between DG harmonics.

Assume a movement as described by equation (9) with four different combinations:

$$x(t) = \sum_k m_k \cdot \sin(2\pi \cdot kf \cdot t). \qquad (9)$$

1) Sinusoidal vibration with k=1
2) Vibration containing 2nd VG harmonic with k=1, 2
3) Vibration containing 3rd VG harmonic with k=1, 3
4) Vibration containing 2nd & 3rd VG harmonics with k=1, 2, 3

To simplify the analysis, the vibration frequency can be normalized to 1 Hz. Following equation (4), with k=1 the amplitude of DG harmonics in the spectrum can be expressed as $H_x(1)$, and the first three DG harmonics will be:

$$H_1(1)=J_1(a_1)$$

$$H_2(1)=J_2(a_1)$$

$$H_3(1)=J_3(a_1). \qquad (10)$$

On the other hand, following equations (3) and (4) by substituting $f_h$=2 and $f_r$=1 to represent a vibration with the 1st and 2nd harmonics for vibration with k=1, 2, the amplitudes of the DG harmonics in terms of $H_x(1)$ will become:

$$H_1(1, 2) = H_1(1)J_0(a_2) + J_{-1}(a_1)J_1(a_2) \qquad (11)$$

$$H_2(1, 2) = H_2(1)J_0(a_2) + J_0(a_1)J_1(a_2)$$

$$H_3(1, 2) = H_3(1)J_0(a_2) + J_1(a_1)J_1(a_2).$$

Figure 3:
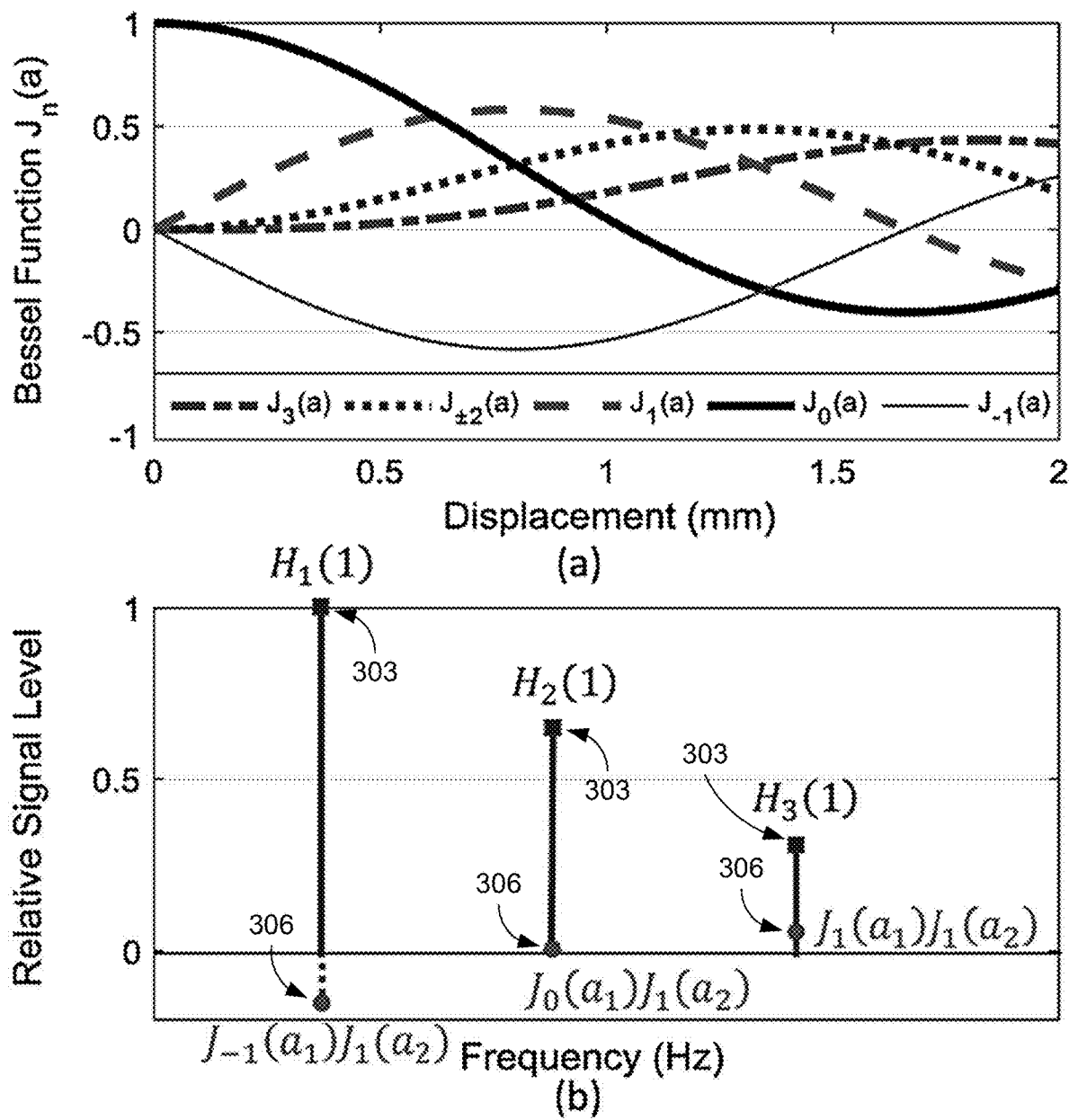
FIG. 3 is an example of a theoretical plot of the value of a Bessel function of the first kind and composition of DG harmonics, in accordance with various embodiments of the present disclosure.

FIG. 3 shows the theoretical plot of the value of the Bessel function of the first kind in 60 GHz: (a) the Bessel function $J_n(a)$ versus vibration displacement, and (b) the composition of DG harmonics for H1, H2 and H3 for vibration with k=1, 2. FIG. 3(a) shows the Bessel function value versus displacement. If the displacement of 2nd VG harmonic (k=2) is relatively small compared to the fundamental vibration (k=1), $J_0(a_2)$ can be regarded as unity, and equation (11) becomes:

$$H_1(1, 2) = H_1(1) + J_{-1}(a_1)J_1(a_2) \qquad (12)$$

$$H_2(1, 2) = H_2(1) + J_0(a_1)J_1(a_2)$$

$$H_3(1, 2) = H_3(1) + J_1(a_1)J_1(a_2).$$

Therefore, as shown in FIG. 3(b), $H_x(1, 2)$ is the summation of the DG harmonic components contributed by the sinusoidal vibration (303) and by the 2nd VG harmonic (306) which modifies the amplitudes of the observed harmonics according to the strength of the 2nd VG harmonic. When $a_2$ is small, $J_1(a_2) \sim a_2$ and equation (12) will approach the case of sinusoidal vibration described by equation (10) as $a_2$ approaches zero.

Figure 4:
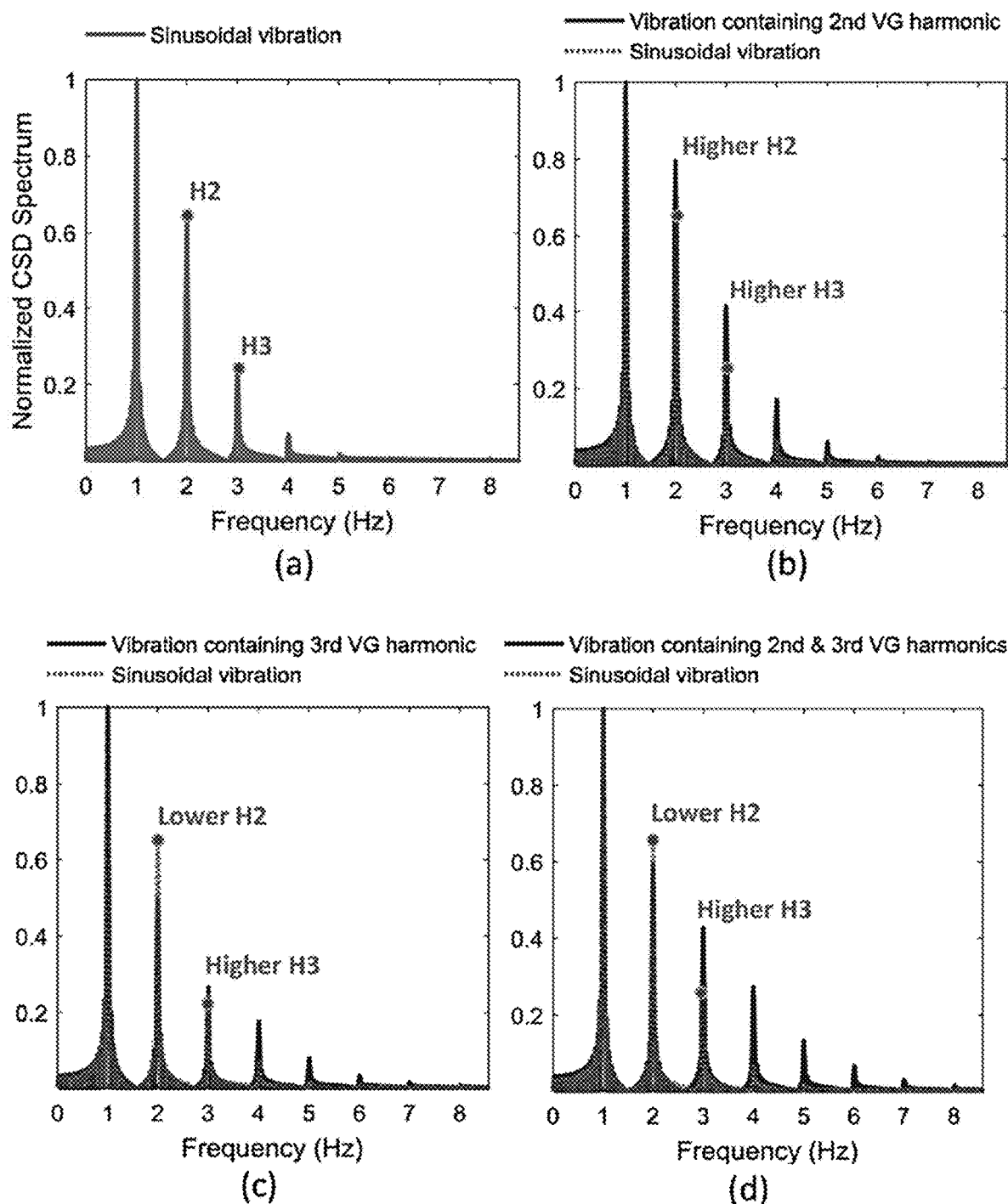
FIG. 4 is an example of normalized CSD spectrums of four simulated vibration patterns compared to the amplitude for the second and third DG harmonics, in accordance with various embodiments of the present disclosure.

Four vibration patterns were examined through simulations. FIG. 4 shows the normalized CSD spectrum of the four vibration patterns with compared amplitude for the second and third DG harmonics (H2 and H3). The spectrum of a sinusoidal vibration is presented in FIG. 4(a) with labeled 2nd and 3rd DG harmonics (H2 and H3) as references in FIG. 4(b) with vibration containing the 2nd VG harmonic, 4(c) with vibration containing the 3rd harmonic, and 4(d) with vibration containing the 2nd and 3rd VG harmonics. If the vibration contains the 2nd VG harmonic, the spectrum obtains higher H2 and H3 as shown in FIG. 4(b), which is also explained by equation (11). If the vibration contains the 3rd VG harmonic, lower H2 and higher H3 can be seen in FIG. 4(c). For vibration containing both 2nd & 3rd VG harmonics, their contributions are combined as shown in FIG. 4(d).

Figure 5:
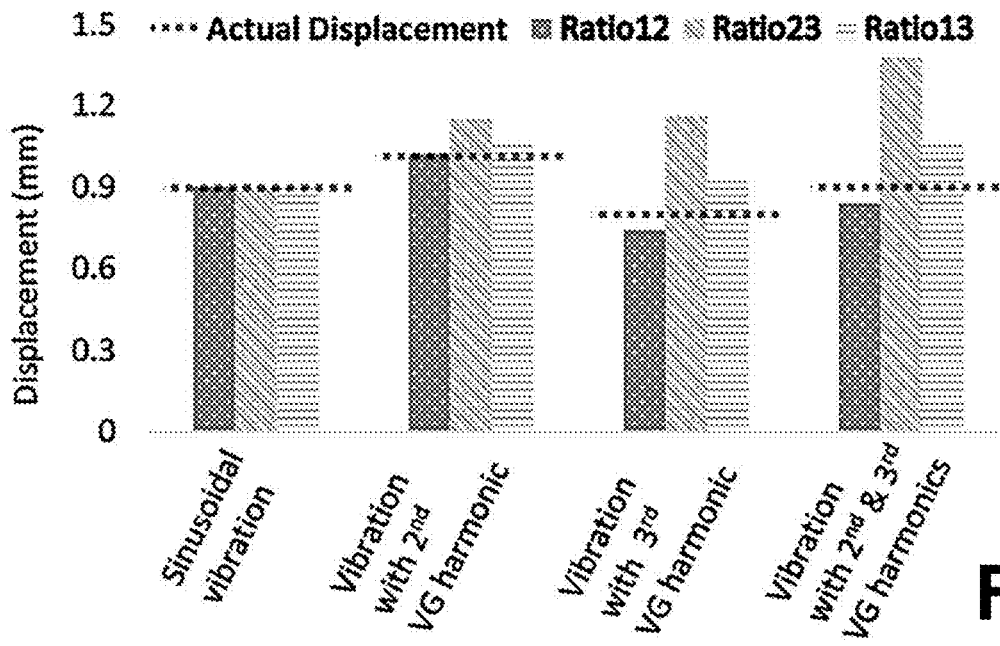
FIG. 5 is an example of displacement extraction with DG harmonic ratios of the simulated vibration patterns of FIG. 4, in accordance with various embodiments of the present disclosure.

FIG. 5 illustrates an example of the displacement extraction with DG harmonic ratios under sinusoidal vibration, vibration containing 2nd VG harmonic, vibration containing $3^{rd}$ VG harmonic, and vibration containing 2nd & 3rd VG harmonics. Actual displacement is the maximum displacement of the vibration and differs from the 0.9 mm displacement of the original sinusoidal vibration due to added harmonic components.

In FIG. 5, the displacement extraction using DG harmonic ratios with fundamental and second (Ratio12), second and third (Ratio23), and fundamental and third (Ratio13) over four vibration patterns are presented. The actual displacement is the maximum displacement of the vibration movement. For sinusoidal vibration, the extracted displacement using three DG harmonic ratios agrees with the actual displacement (0.9 mm). The smallest displacement measurement error of those non-sinusoidal vibrations is obtained by using only Ratio12. It can also be observed from FIG. 5 that when the vibration contains more VG harmonics, it will create larger deviations by using Ratio13 and Ratio23. Since the odd-order VG harmonics significantly distort the signal compared to even-order VG harmonics, the asymmetric waveform will create a larger deviation from its original signal. Therefore, choosing the even-order DG harmonics for displacement acquisition is expected to have smaller error. Another consideration is that H3 could be small due to tiny displacement, and Ratio13 have larger error. As a result, using Ratio12 is more reliable not only because it has the smallest average deviation error, but also the 1st and the 2nd harmonics are the two strongest peaks on the spectrum which are more resistant to noise.

The minimum displacement that radar can accurately measure is determined by the carrier frequency. With a higher frequency and shorter wavelength, the nonlinear phase demodulation effect can be significant and the DG harmonics become more obvious, making the displacement acquisition easier. Small animals like laboratory rats have faster RR and HR, which are associated with smaller chest-wall displacements. In order to detect rat's cardiorespiratory movement, a 60 GHz radar was used for its capability of detecting small vibrations and producing stronger DG harmonics.

Figure 6:
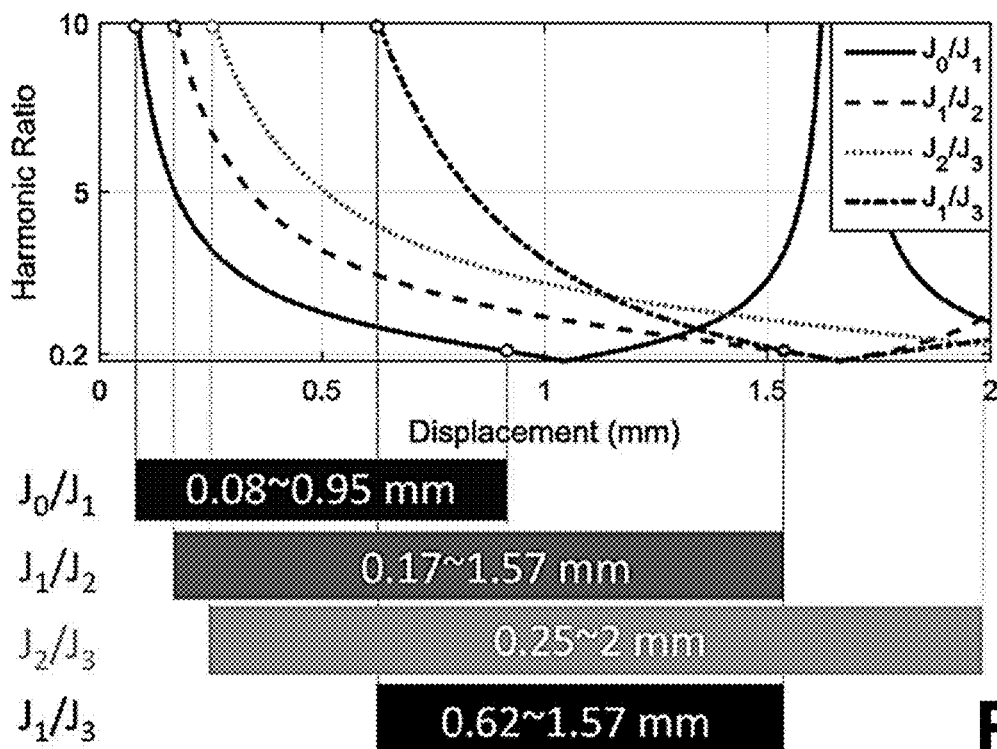
FIG. 6 is an example of theoretical DG harmonic ratio versus displacement, in accordance with various embodiments of the present disclosure.

Radar Detection Range for Sub-millimeter Displacement Acquisition. In order to extract the displacement of cardiorespiratory movement, several DG harmonic ratios should be obtained first. The displacements can be calculated from the ratios of Bessel functions given in equations (6) and (7). The theoretical DG harmonic ratio versus displacement is shown in FIG. 6, and four ratio traces are presented with the 60 GHz radar detection range indicated with the measurable ratios. Since it is not accurate to measure too small or too large of a ratio, the measurable ratio from 0.2 to 10 was selected, with the detection ranges with different ratios also indicated. The $J_0/J_1$ can be used for heartbeat displacement acquisition, with a detectable range that can cover down to 0.08 mm. By using $J_1/J_2$, it is possible to detect respiration displacement down to 0.17 mm. The $J_2/J_3$ has the widest detection range, however, it may suffer from a large deviation if movement contains VG harmonics. If the rat's respiration displacement is in the normal range from 0.62 to 1.57 mm without any drug effect, both $J_1/J_2$ and $J_1/J_3$ can be used to increase the detection accuracy.

Figure 7A:
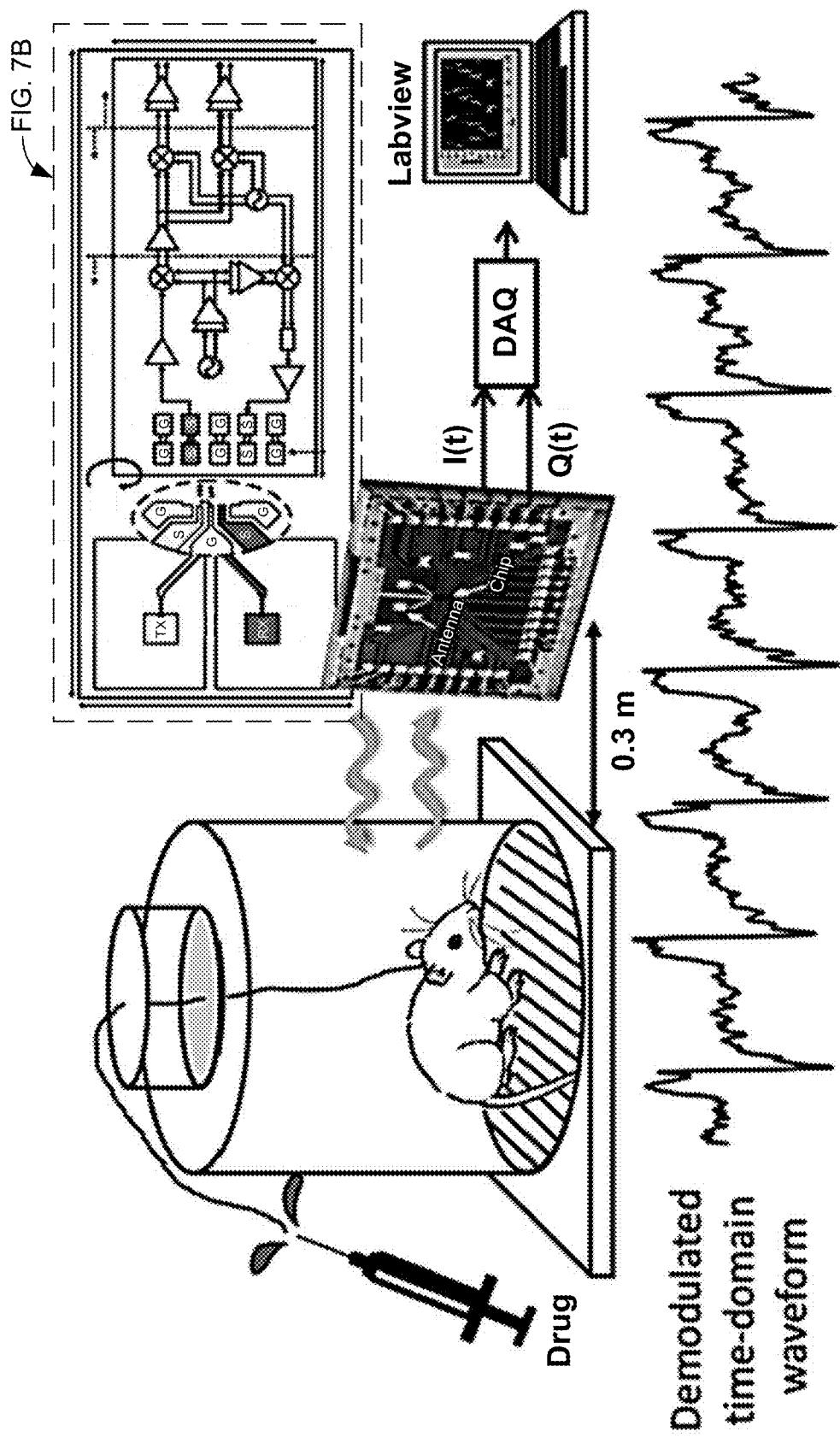
FIGS. 7A and 7B is an example of an experimental setup for measuring cardiorespiratory movement of a laboratory rat, in accordance with various embodiments of the present disclosure.
Figure 7B:
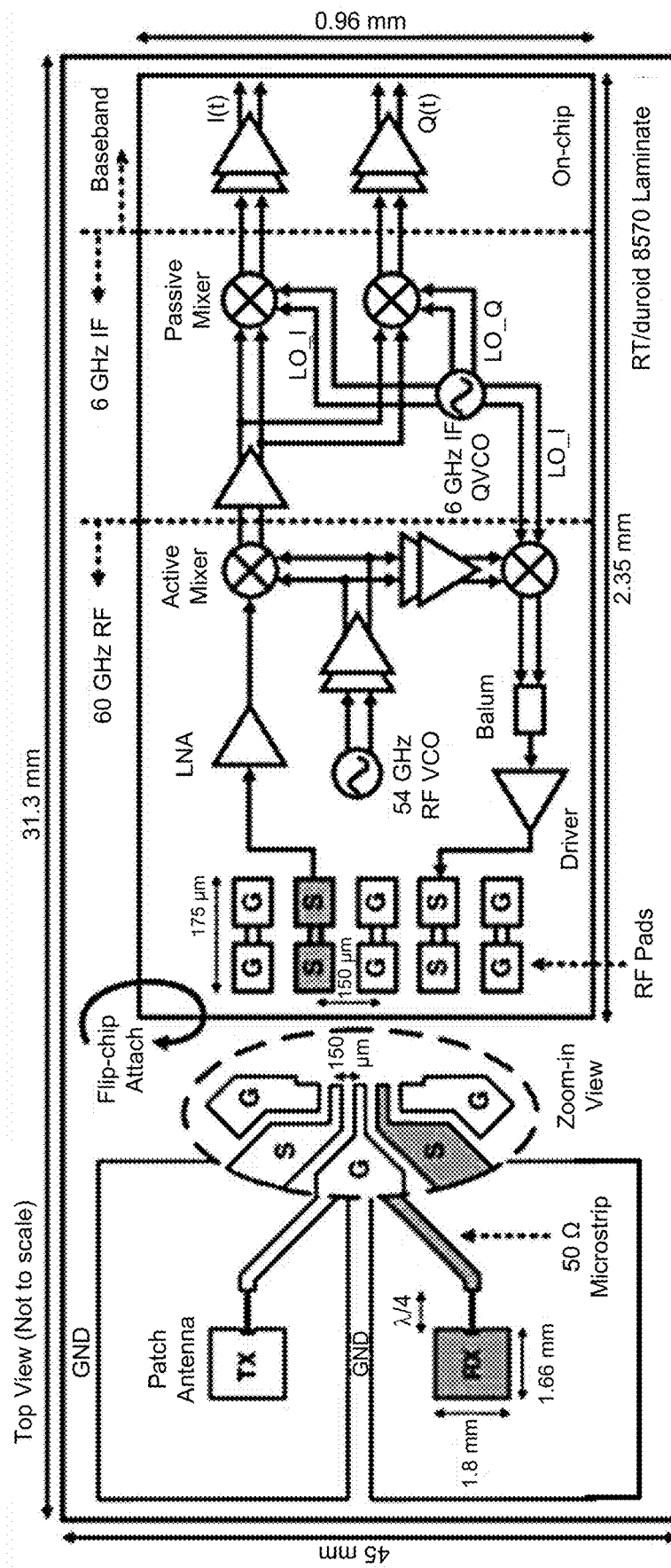

Experimental Results with 60 GHz CMOS Radar. Referring to FIGS. 7A and 7B, shown is a graphical representation of an experimental setup for measuring cardiorespiratory movement of a laboratory rat in a whole body plethysmography chamber. The experimental setup used a 60 GHz CMOS radar for non-contact measurement of the laboratory rat's cardiorespiratory movement. An arterial catheter (e.g., FC-M-37L, Braintree Scientific Inc., Braintree, MA, USA) was placed in the femoral artery of an anesthetized adult rat and then the rat was placed in the whole body plethysmograph (e.g., chamber volume 4 L; Buxco Electronic Inc., Wilmington, NC, USA). The arterial catheter was threaded through the top of the chamber and connected to a calibrated pressure transducer (e.g., Stoelting, Woodale, Ill., USA). Oxygen (100%) was delivered to the chamber at a rate of 2 L/min. The plethysmograph was fitted with a pressure transducer (e.g., TRD5700Buxco Electronic Inc.). The arterial pressure signal and analog output from the plethysmograph pressure transducer were recorded online (e.g., with a sampling frequency of 200 Hz) via a data acquisition interface (e.g., Power1404, Cambridge Electronic Design (CED), Cambridge, U.K.) connected to a computing device (e.g., a laptop computer) equipped with a complimentary data analysis software system (e.g., Spike2, CED, Cambridge, U.K.). Off-line Spike2 subroutines were used to identify peaks in the arterial pressure and plethysmograph pressure traces, which corresponded to the time of peak systolic arterial pressure and peak inspiratory pressure, respectively. HR and RR were calculated as: 60/(peak-to-peak interval). Respiratory movement, blood pressure (BP) and HR were simultaneously recorded with Spike2 software (200 Hz sampling rate) for reference. The radar system included a 60-GHz flip-chip transceiver chip (90-nm CMOS) integrated with patch antennas on a RT/duroid 5870 laminate, and powered by a battery. The power consumption was 377 mW at 1.2-V power supply, and the transmit power was 0 dBm.

The radar was placed at 0.3 m from the plethysmograph to detect the rat's movements, and the received quadrature signals were sampled by a National Instruments data acquisition board (DAQ) and before being sent to, e.g., a laptop for signal processing. Anesthesia was induced with urethane (1.3 mg/kg). In addition to measuring an anesthetized rat using radar to extract both frequencies and displacements of its respiration and heartbeat using the method previously described, two drug tests with raised BP (phenylephrine) and dropped BP (atropine) for longer monitoring period were also performed. A Labview program concurrently recorded the rat's cardiorespiratory movement and the output was compared with simultaneous recordings made with the Spike2 software. For healthy adult rats, the typical RR ranges from 0.5-2.2 Hz and HR ranges from 5-7 Hz. A Butterworth band-pass filter was set from 0.1 Hz to 13 Hz to eliminate the DC and high frequency interference that introduced from surrounding noise and wire electronic noise.

Figure 8:
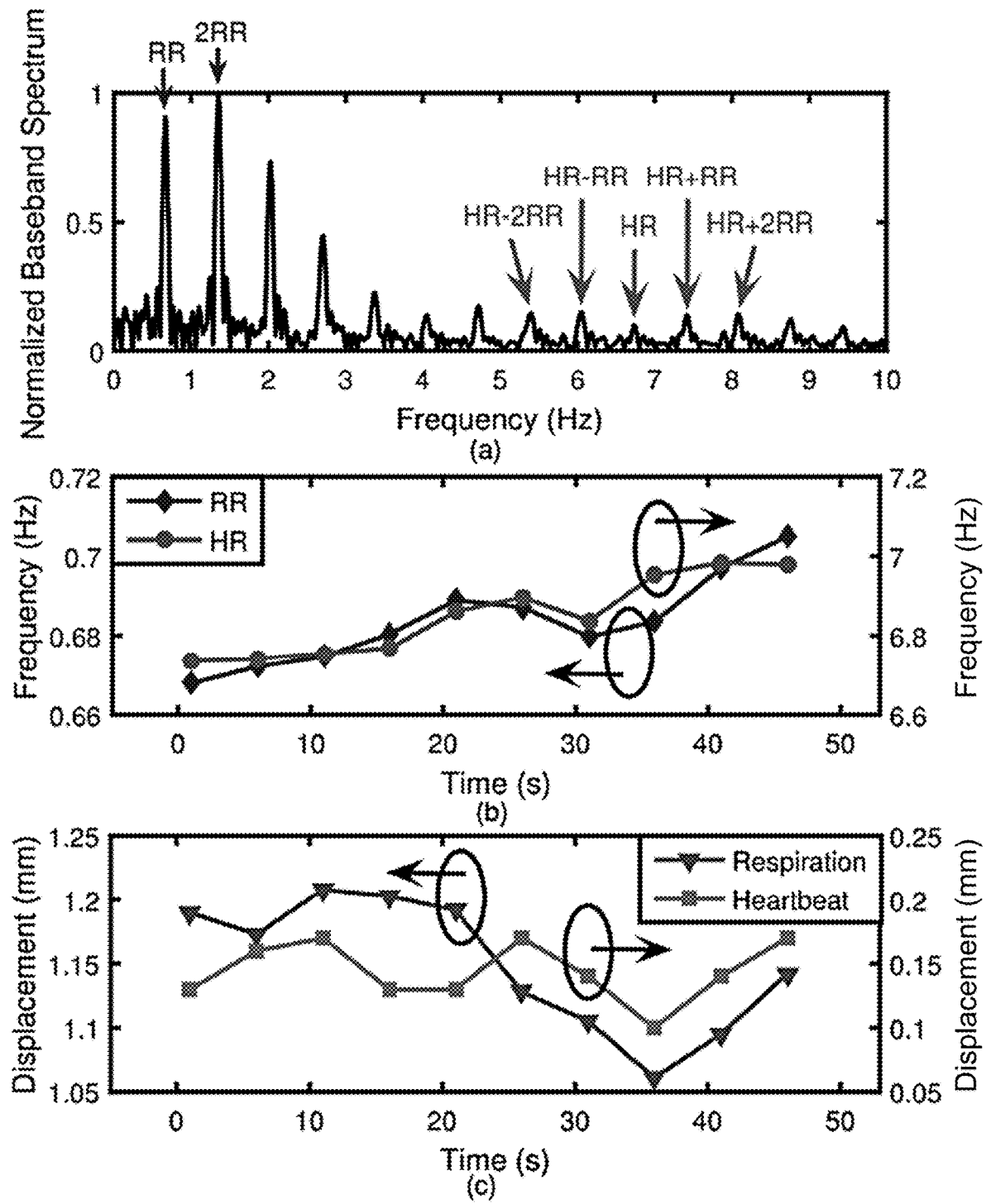
FIG. 8 is an example of results from the cardiorespiratory movement measurements of a laboratory rat using the experimental setup of FIGS. 7A and 7B, in accordance with various embodiments of the present disclosure.
Figure 9:
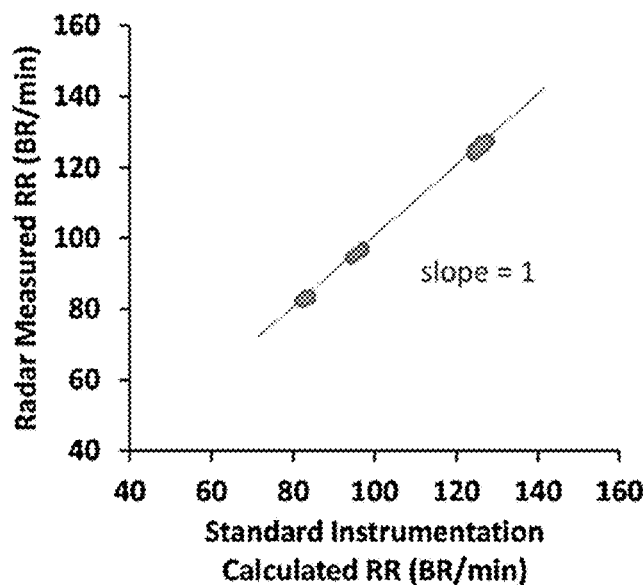
FIG. 9 is a table illustrating the measured rate and calculated displacement of the results of FIG. 8, in accordance with various embodiments of the present disclosure.

Three experiments were conducted when measuring the rats under anesthesia. It was found that the average error for either the RR or HR comparison was less than 0.1% in the three experiments. FIG. 8 illustrates the results of the cardiorespiratory movement measurements of experiment #1. FIG. 8(a) shows the normalized measured baseband spectrum at 0-15 s. By utilizing the DG harmonics generated in the spectrum as labeled, the measured rate and calculated displacement can be determined. The results are listed in the table of FIG. 9. The ratio of $H_{RR}/H_{2RR}$ was used for calculating respiration displacement, and $H_{RR}/H_{HR-RR}$ and $H_{2RR}/H_{HR-2RR}$ were both chosen for heartbeat displacement extraction.

Applying the CSD technique, the received complex signal was generated by combining I and Q baseband outputs. Since the displacement was comparable to the wavelength, the nonlinear Doppler phase modulation effect was significant and the rat's cardiorespiratory signal contains harmonics and intermodulation products from both respiration ($f_r$) and heartbeat ($f_h$), expressed as:

$$H_x = \left| \sum_{p=-\infty}^{\infty} \sum_{q=(x-f_h p)/f_r} J_p(a_h) J_q(a_r) \right| \cdot \left| e^{j2x\pi t} \right|, \quad (13)$$

where $a_h = 4\pi m_h/\lambda$ and $a_r = 4\pi m_r/\lambda$, and $m_h$ are respiration and heartbeat displacement, J(a) is the first kind Bessel function, x Hz represents the harmonic frequency, p and q are integers, and is the carrier wavelength.

The harmonics shown in the baseband spectrum of FIG. 8(a) can be grouped into two categories: the respiration and its harmonics, and the frequency mixing products of RR and HR. The respiration harmonics are labeled and the frequency mixing products are identified and used to determine the correct HR peak. Similar to intermodulation or frequency mixing, the HR mixes with RR and its harmonics, resulting in the mixing products in the detected spectrum. It should be noted that the frequency mixing products are symmetrically centered around the HR peak because they share the same Bessel function coefficient on $a_h$. The measured RR and HR were 0.66 Hz and 6.73 Hz, respectively.

After the RR and HR are extracted, the $m_h$ and $m_r$ can be obtained. The ratio of the two strongest harmonics in the spectrum, $H_{0.66}/H_{1.35}$, was used for calculating the $m_r$. For heartbeat displacement, two harmonic pairs, $H_{1.35}/H_{5.39}$ and $H_{0.66}/H_{6.04}$, were chosen because they contain the information involving different $J_p(a_h)$ with the same $J_q(a_r)$. Therefore, the same $J_q(a_r)$ can be cancelled out by taking the ratio, leaving the $J_p(a_h)$ only for calculating $m_h$.

FIG. 8(b) shows the monitored RR and HR records over the 47 s observation time and 8(c) shows the displacement variations of both respiration and heartbeat versus time. Each data point was obtained by using a 15 s time window. The variations of both rates and displacements within the measurement time can be observed. Both RR and HR show an increasing trend within the 47 s recording time, in which each data point represents a 15 s time slot.

Figure 10:
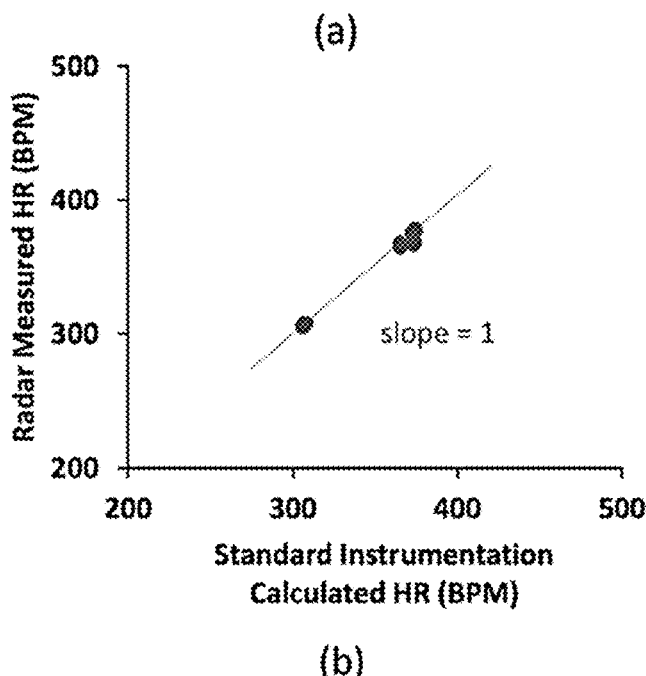
FIG. 10 is an example of correlation diagrams of instrument-recorded data and the radar-recorded data for test measurements using the experimental setup of FIGS. 7A and 7B, in accordance with various embodiments of the present disclosure.

Experiment #2 was performed on three different rats on different dates under anesthesia. FIG. 10 shows the correlation diagram of instrument-recorded data and the radar-recorded data for the three test subjects. FIG. 10(a) is a plot the respiration rate (RR) and FIG. 10(b) is a plot of the heart rate (HR). The variability in HR and RR may be attributed to how the urethane was delivered to the test subjects. The average error of either the RR or HR comparison ranged between 0.057% and 0.33%.

Figure 11:
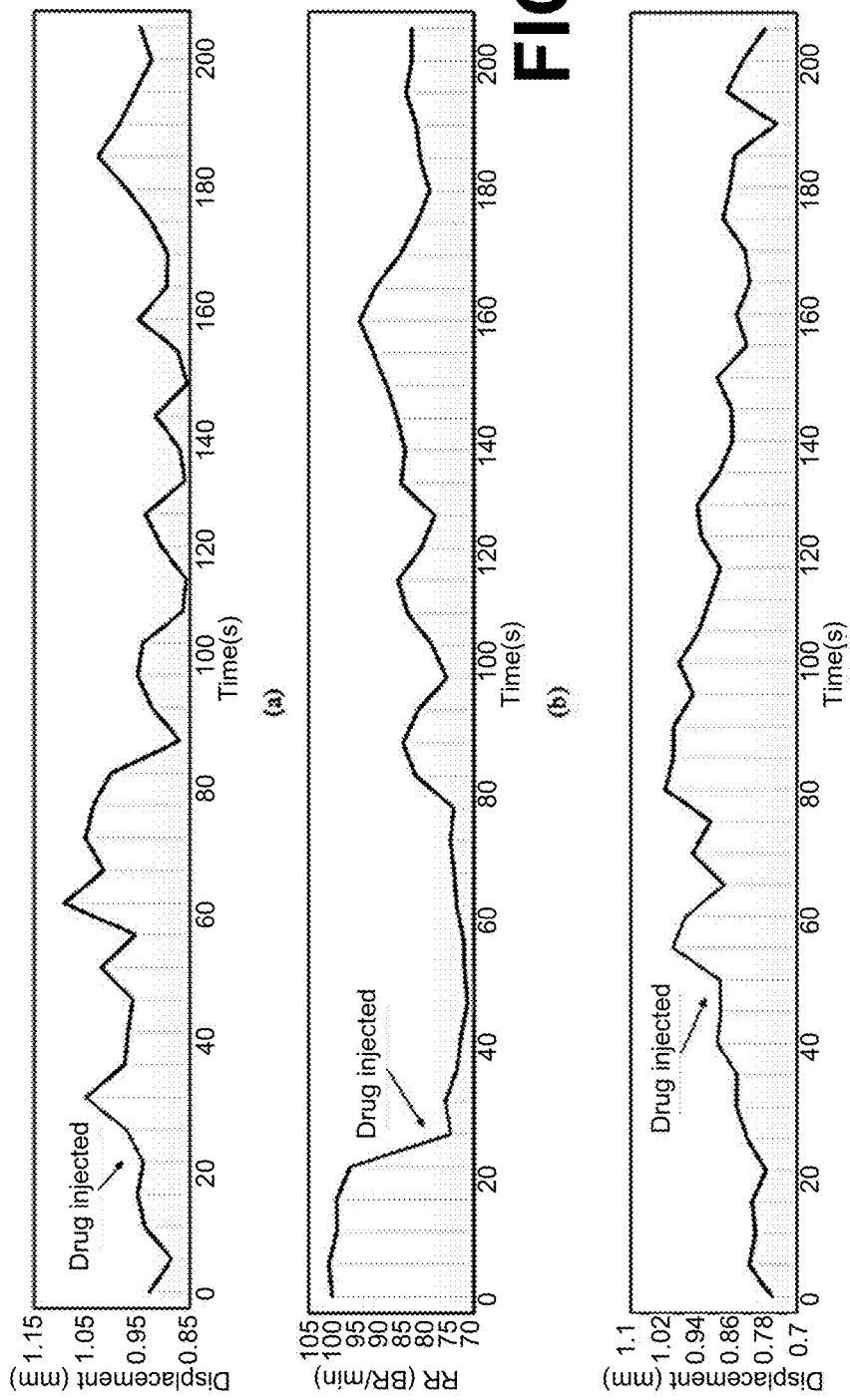
FIGS. 11 and 12 are examples of respiratory displacement variation and RR variation for anesthetized laboratory rats, in accordance with various embodiments of the present disclosure.
Figure 12:
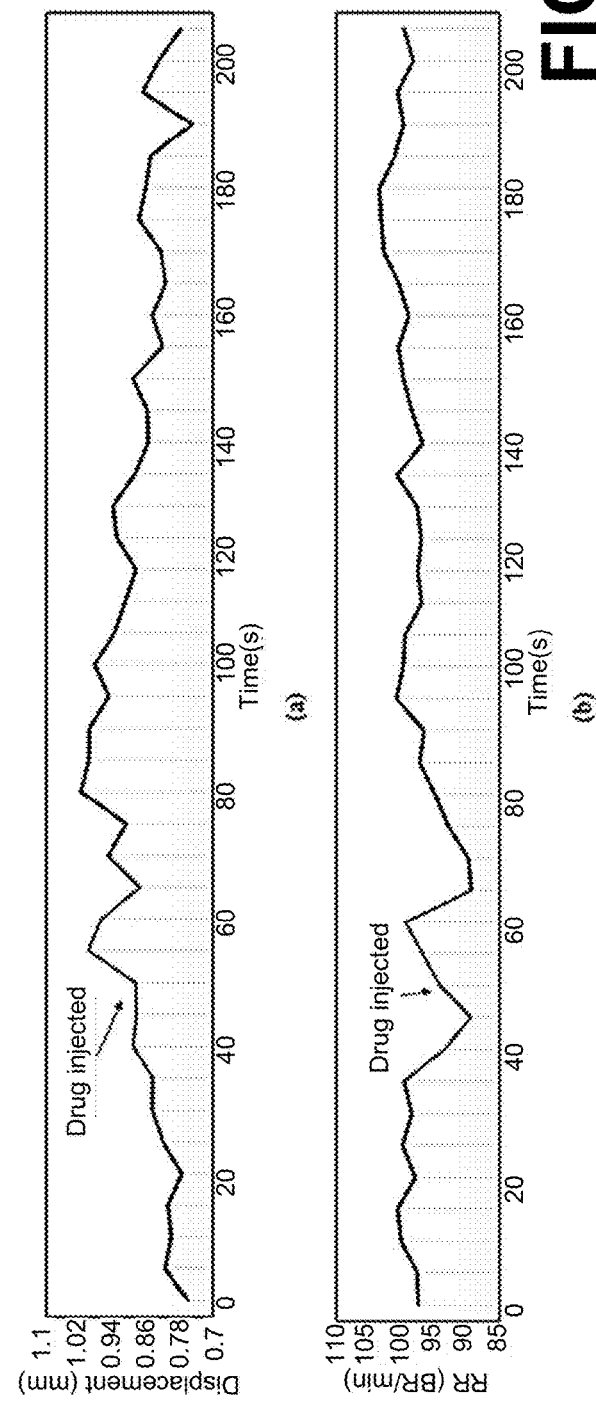

Experiment #3 was a drug test using two different drugs. Since a body needs some settling time to react after drug injection, and the raised/dropped RRs varied with time significantly, the time window was shorten from 15 s to 5 s to see the instant changes. FIGS. 11 and 12 show the respiratory movement variations with a 200 s total observation time, with the drug-injected points labeled. FIG. 11 illustrates the (a) respiratory displacement variation and (b) RR variation for phenylephrine. The reflexively slowed HR and RR were induced with phenylephrine which raised the BP. It can be observed from FIG. 11(b) that the RR dropped from 100 to 75 Breath/min (BR/min) after injection and stayed relatively unchanged for 50 s. During the 50 s period, the displacement fluctuated and increased from minimum 0.9 to maximum 1.092 mm which increased by 20%. After that, the RR slowly recovered to its normal range with constant fluctuations in displacement. FIG. 12 illustrates the (a) respiratory displacement variation and (b) RR variation for atropine. The dropped BP was induced with atropine. The drug took around 20 s to activate as color-labeled. RR slowly sped up when the drug became effective, and respiratory displacement slowly decreased by 26% following the raised RR.

It was found that the HR amplitude became weaker if a drug was induced in the experiment. The drug effect makes respiratory movement much larger which suppress the HR amplitude in the detected spectrum. In addition, the large respiratory displacement will also make $J_0$ in the HR-mixing products close to the zero-crossing point, which further degrades the HR amplitude in spectrum.

Adaptive HCNDF for Removing Respiration Harmonics

Figure 13A:
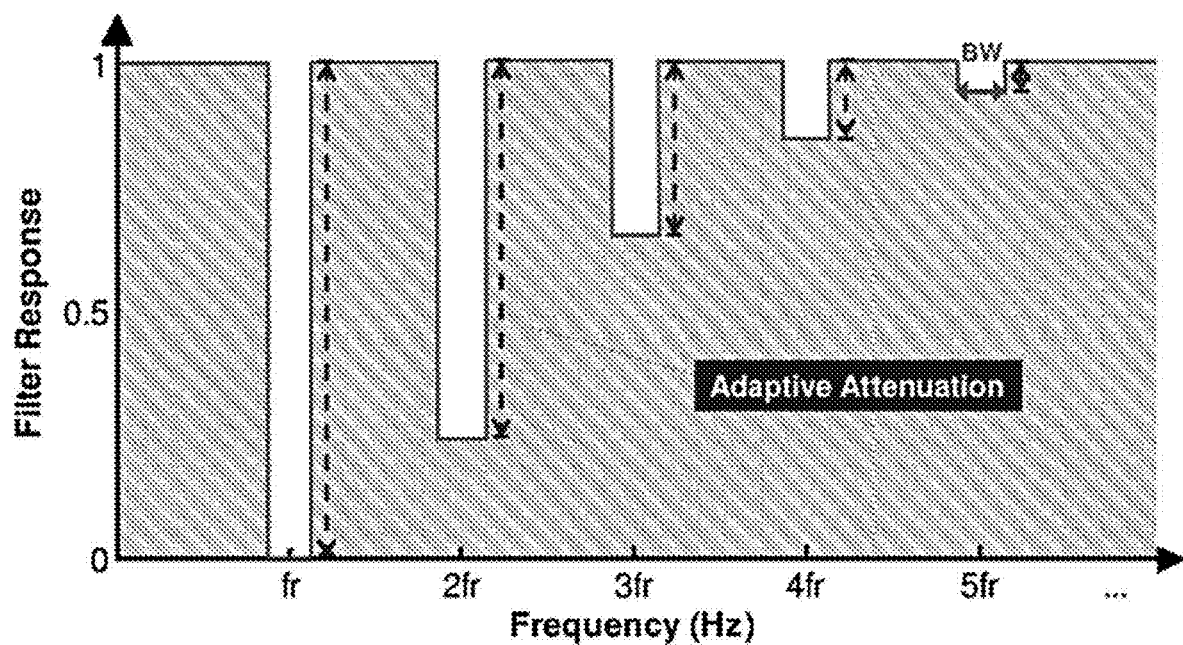
FIGS. 13A and 13B illustrate an example of an adaptive harmonics comb notch digital filter (HCNDF), in accordance with various embodiments of the present disclosure.

Referring next to FIG. 13A, shown is an example of the adaptive harmonics comb notch digital filter (HCNDF), which comprises multiple notch frequencies at respiration and its harmonics, using the determined respiration rate (RR) and extracted displacement. Unlike a comb filter, the HCNDF is based on a Fourier transform of the detected signal that utilizes the harmonics generated in the spectrum due to the demodulation method, and extract the displacement of respiratory movement by the ratio of harmonic amplitudes. After applying the filter in the original spectrum, the respiration harmonics can be removed without removing the heartbeat signal. Experiments were conducted using a 60-GHz CMOS radar. Since a rat's vital sign movement is much smaller compared to human vital sign movement, 60 GHz radar which is capable of detecting small vibrations and producing stronger harmonics in nonlinear Doppler phase demodulation is used in this work. Measurements of conscious rat, anesthetized rat, and drug-induced high blood pressure (BP) rat with and without the HCNDF are compared to verify the proposed technique.

The detected baseband signal in I and Q channels can be combined by the CSD method, and expressed as:

$$B(t) = I + jQ = \cos\left[\frac{4\pi x_h(t)}{\lambda} + \frac{4\pi x_r(t)}{\lambda} + \phi\right] \quad (14a)$$

-continued $$= J_0(a_h) \sum_{q=-\infty}^{\infty} J_q(a_r) \cdot e^{j2\pi(f_r q)t} \cdot e^{j\phi} + \quad (14b)$$

$$J_1(a_h) \sum_{q=-\infty}^{\infty} J_q(a_r) \cdot e^{j2\pi(f_r q + f_h)t} \cdot e^{j\phi} + \dots . \quad (14c)$$

The equation comprises RR and its harmonics, and their mixing products with HR as (14b) and (14c), respectively. J(a) is the first kind Bessel function, $a_h = 4\pi m_h/\lambda$ and $a_r = 4\pi m_r/\lambda$, $m_r$ and $m_h$ are displacements of respiration ($f_r$) and heartbeat ($f_h$), p and q are integers, $\lambda$ is the carrier wavelength of radar signal, and $\phi$ is the total residual phase which can be neglected due to the constant envelope of unity.

After taking the FFT of the baseband signal, $f_r$ can be determined. Since the respiratory movement is not an ideal single tone or symmetric movement, the first and second harmonics can be chosen for $m_r$ extraction which can be expressed as:

$$m_r = \frac{|J_0(a_h)J_1(a_r)|}{|J_0(a_h)J_2(a_r)|} = \frac{|J_1(a_r)|}{|J_2(a_r)|}. \quad (15)$$

Figure 14:
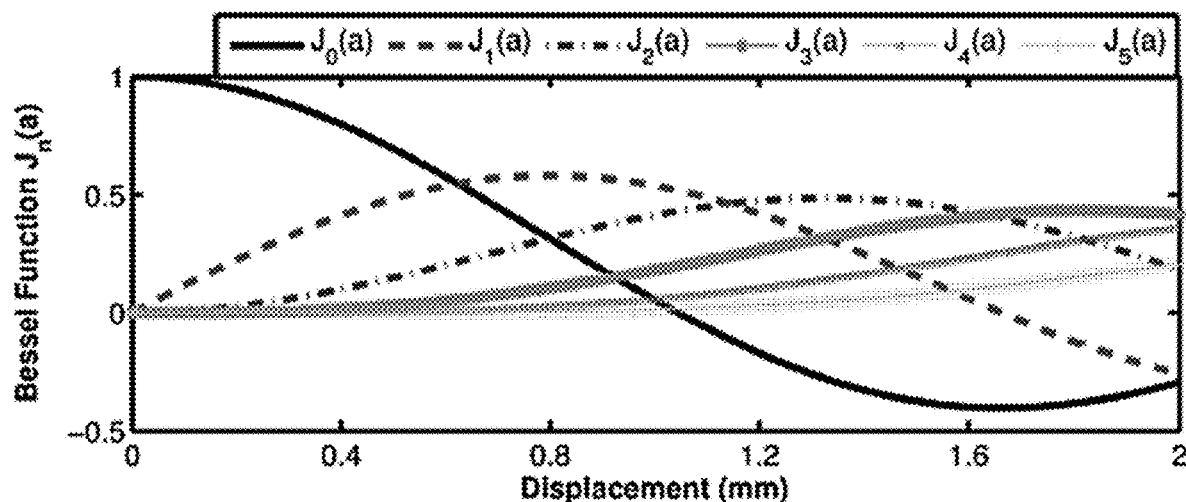
FIG. 14 is an example of a theoretical plot of a nonlinear Doppler phase demodulation effect, in accordance with various embodiments of the present disclosure.
Figure 14:
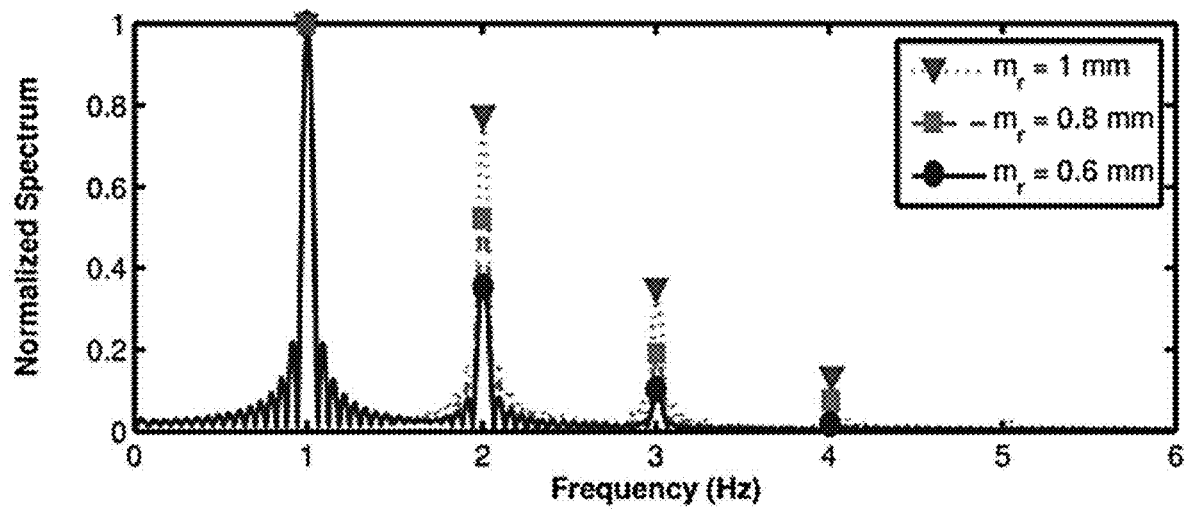

FIG. 14 shows the theoretical plot of the 60-GHz nonlinear Doppler phase demodulation effect: (a) the Bessel function $J_n(a)$ versus vibration displacement, and (b) the of the 60 GHz nonlinear Doppler phase demodulation effect. The Bessel function versus vibration displacement at 60 GHz is shown in FIG. 14(a). If the displacement exceeds 1.15 mm, $J_2$ will be larger than $J_1$, which will result in a higher second harmonic and lower first harmonic. FIG. 14(b) shows the harmonic amplitude varied with displacements. The spectrum is normalized and is independent of the measurement distance between radar and target; hence no calibration is needed.

Figure 13B:
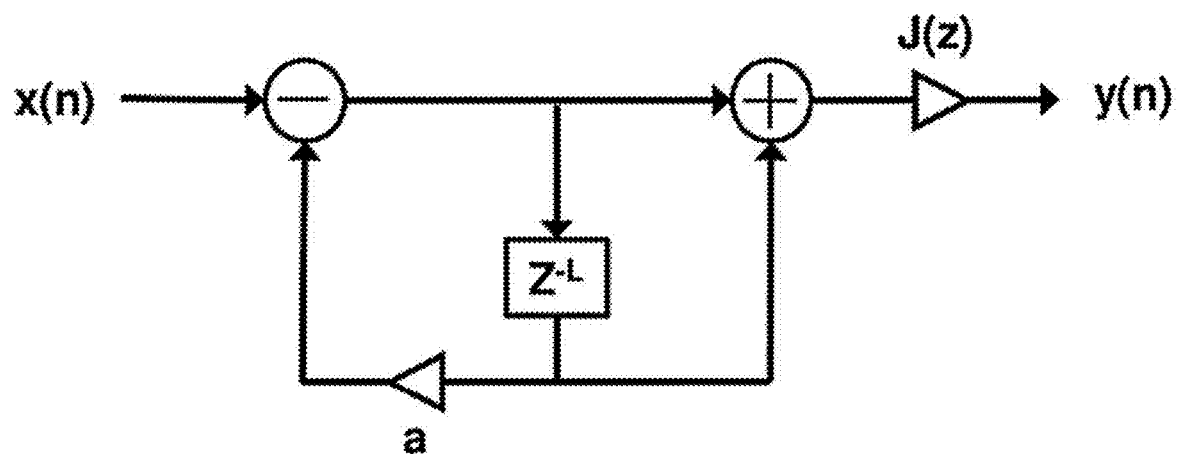

Using the respiration spectrum to design a comb notch filter, the notch attenuation at each notch frequency is adaptive to the respiration displacement. FIG. 13B shows an example of an implementation of the adaptive HCNDF. The difference equation describing the filter can be expressed as:

$$y(n) = J(z)[x(n) + x(n-L)] - ay(n-L), \quad (16)$$

where a is the feedback gain which determines the bandwidth (BW), and J(z) is a function of the notch attenuation gain contributed from the Bessel coefficients of respiration, which can be expressed as:

$$J(z) = \sum_{i=1}^{L} J_i(a_r). \quad (17)$$

The transfer function with z-transform of the HCNDF can be expressed as:

$$H(z) = \frac{J(z)(1+z^{-L})}{1+az^{-L}}. \quad (18)$$

The filter has poles to introduce a resonance in the vicinity and reduce the BW of the notch, and zeros at:

$$z = e^{j\omega k}, k = 0, 1, 2, \dots, L-1. \quad (19)$$

The frequency response of the filter as shown in FIG. 13A that $|H(e^{j\omega})|$ has L notches at $\omega_k = (2k+1)\pi/L$ in the frequency band, and the first notch occurs at $\omega_0 = 2\pi f_r$.

After applying the HCNDF in the detected signal, the output of the filter can be expressed as:

$$Y(t) = J_1(a_h) \sum_{q=-\infty}^{\infty} J_q(a_r) \cdot e^{j2\pi(f_r q + f_h)t} \cdot e^{j\phi} + \quad (20)$$

$$J_2(a_h) \sum_{q=-\infty}^{\infty} J_q(a_r) \cdot e^{j2\pi(f_r q + 2f_h)t} \cdot e^{j\phi} + \dots .$$

Compared to the equation of (14a-14c), the RR harmonics (14b) is removed, only the HR mixing products with RR remain. The HCNDF will not remove the heartbeat even if the HR is overlapping with the RR harmonics. The BW of the filter stop-band can depend on the observation window length. If the observation interval of the signal is limited, the spectrum resolution will be low and suffer from spectral leakages. As a result, the BW can be adjusted following the resolution to filter out the unwanted harmonics.

Figure 15:
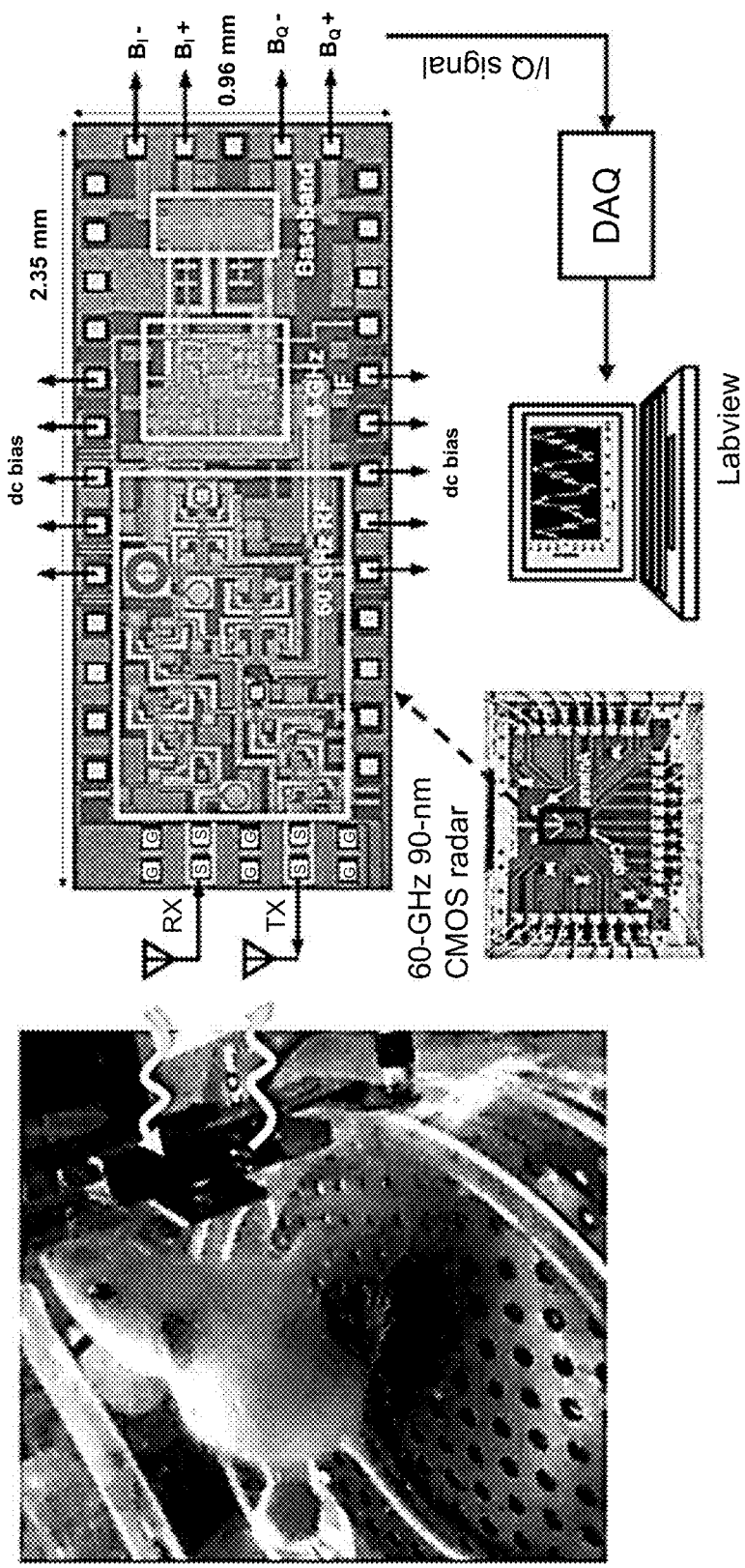
FIG. 15 is an example of the experimental setup used for measurements of a laboratory rat, in accordance with various embodiments of the present disclosure.

Experimental Results with 60 GHz CMOS Radar. Referring to FIG. 15, shown is a graphical representation of the experimental setup used for measuring the laboratory rat in a whole body plethysmography chamber. The experiment uses the 60-GHz CMOS radar for noncontact measuring the laboratory rat's cardiorespiratory movement. As described above, the system includes a 60 GHz flip-chip radar transceiver (90 nm CMOS) and two patch antennas for TX and RX on RT/duroid 5870 laminate which is powered by a battery. Transmit power is 0 dBm, and the total power consumption is 377 mW at 1.2 V power supply.

Following instrumentation, the rat was placed in the whole body plethysmograph and an arterial catheter was placed in the femoral artery. BP, HR, RR and movement were simultaneously recorded with Spike2 software (200 Hz sampling rate per channel) as reference. The radar was placed at 0.3 m from the cage to detect the rat's vital signs, and the received I/Q signals were sampled by a data acquisition model and sent to a laptop for processing.

Measurements were conducted under three scenarios for comparison: (a) with a conscious rat with random body movement, (b) with an anesthetized rat induced with urethane, and (c) with an anesthetized rat with high BP (low or dropped HR) induced with phenylephrine. The observation time was 20 s, and the BW of the HCNDF was set to 0.25 Hz to ensure the harmonics could be properly removed.

Figure 16A:
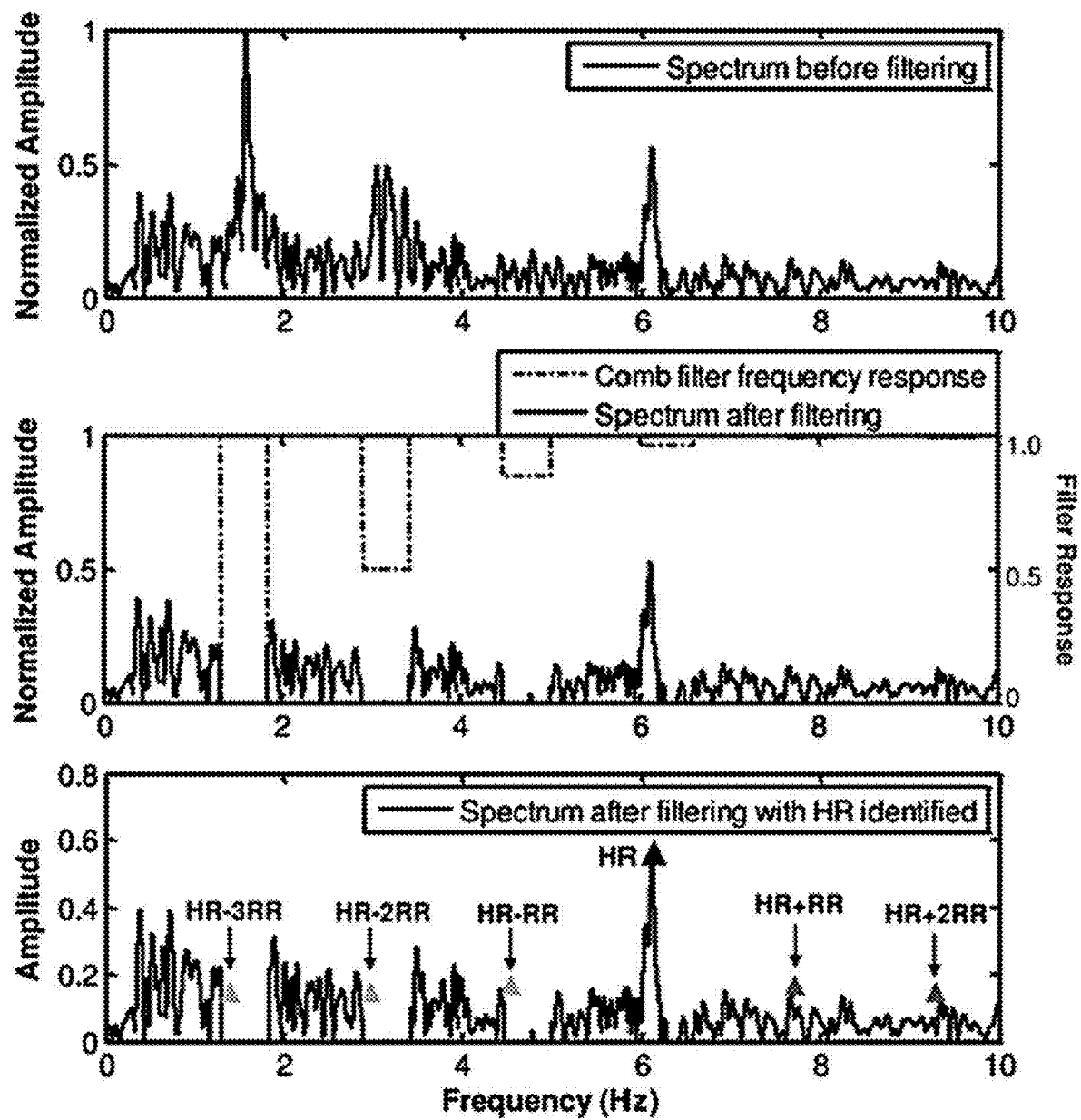
FIGS. 16A through 16C are examples of results from measurements of laboratory rats using the experimental setup of FIG. 15 and the HCNDF, in accordance with various embodiments of the present disclosure.
Figure 16B:
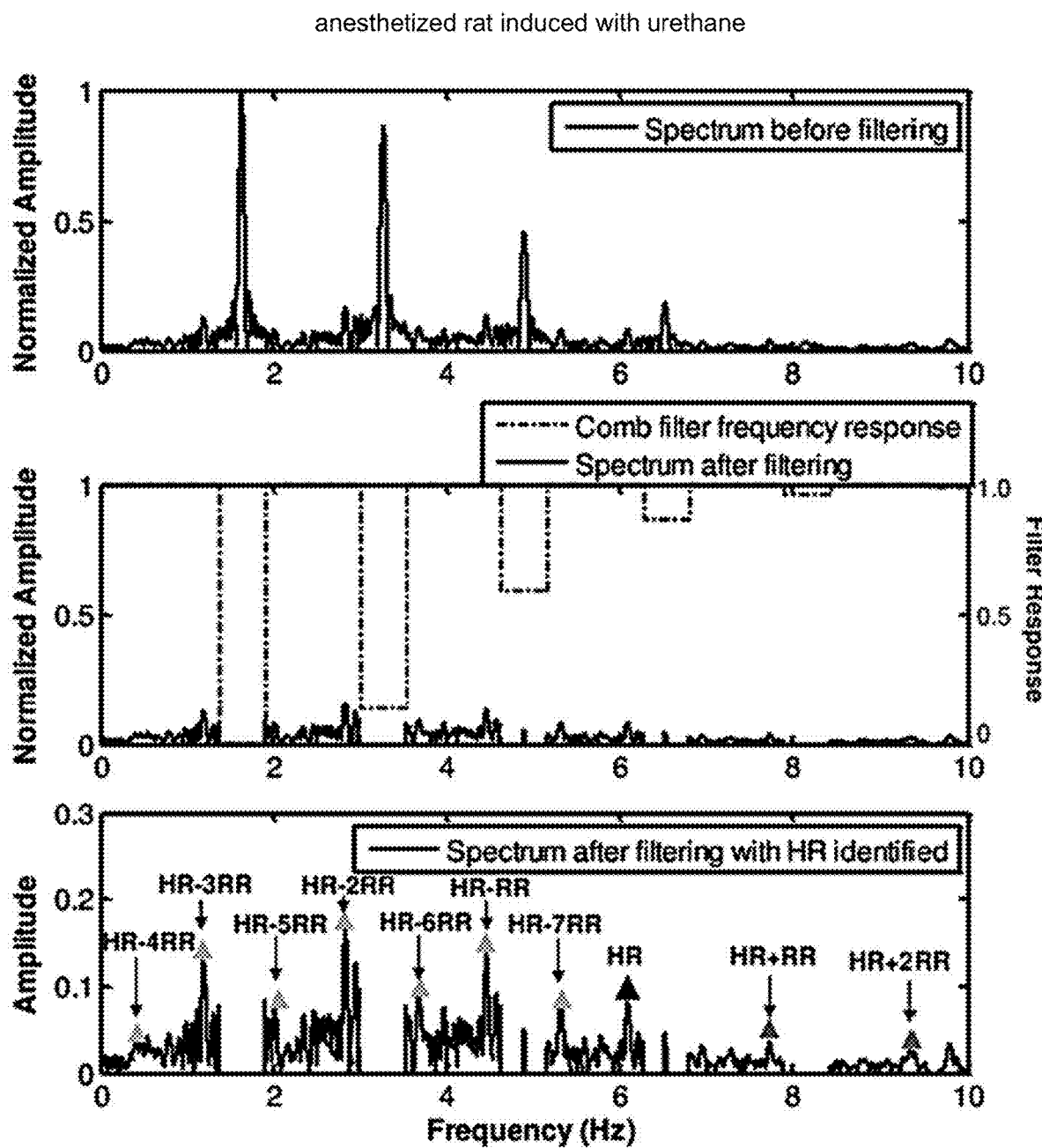
Figure 16C:
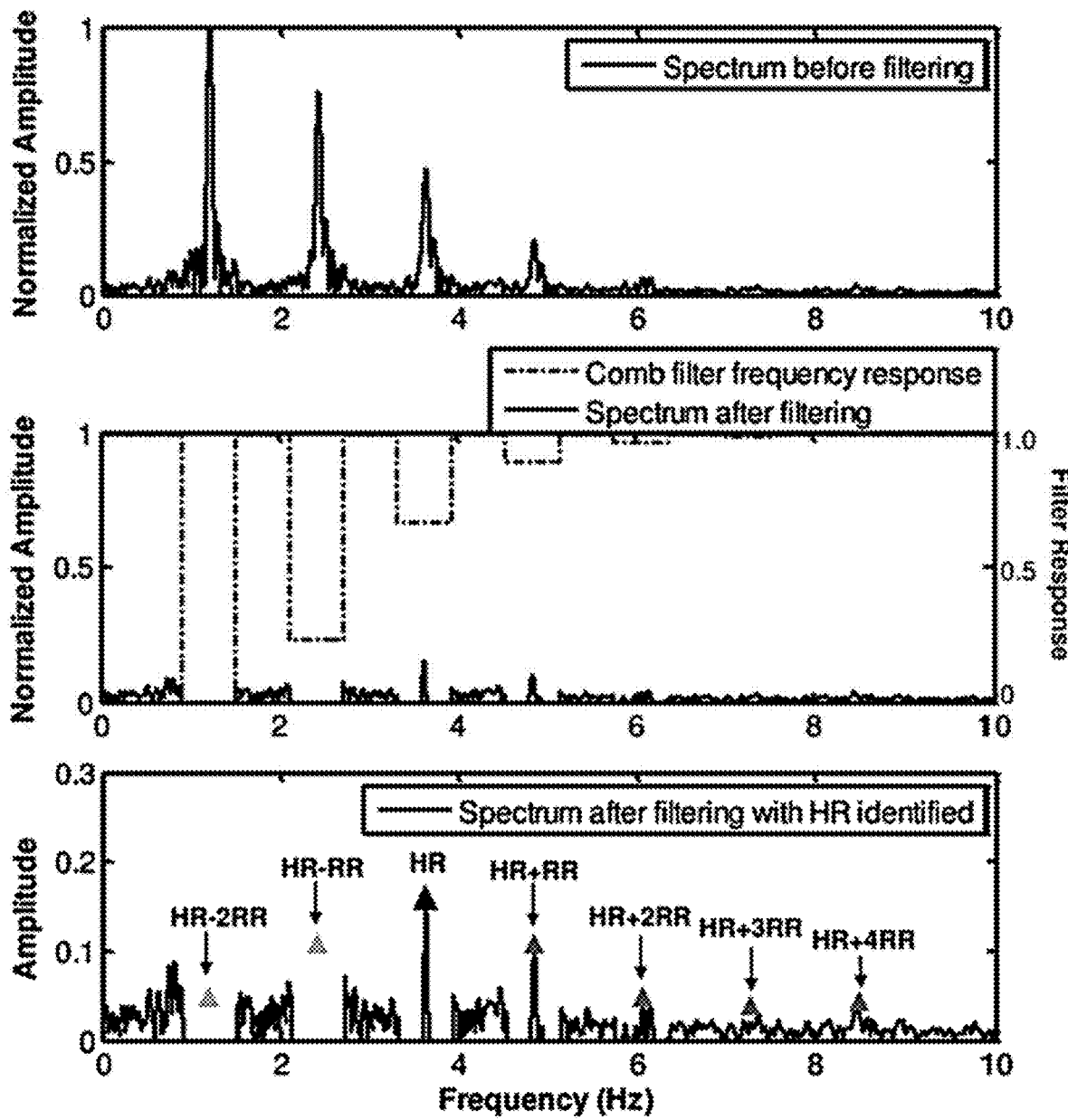

FIGS. 16A, 16B and 16C show the measurement spectrums under the different test scenarios with the radar-recorded spectrum before filtering shown in the top plots, the NCNDF frequency response and spectrum after filtering shown in the middle plots, and the spectrum after filtering with HR identified shown in the bottom plots. As can be seen from FIG. 16A, the radar-measured RR for the conscious rat was 1.58 Hz and the calculated $m_r$ was 0.742 mm. Using the extracted RR and displacement from radar-recorded data for the anesthetized rat, the HCNDF was constructed and implemented as FIG. 16B. The radar-measured HR was 6.1 Hz. In this test, the signal level was not good enough to suppress the noise floor since the rat was conscious with random body movement.

Compared with the conscious rat, anesthesia of the rat resulted in larger chest-wall movement so the nonlinear effect was more significant. The radar-measured RR was 1.632 Hz and the calculated $m_r$ was 1.061 mm. FIG. 16B shows the radar-measured HR at 6.088 Hz. In this test, the HR mixing products in low frequency were enlarged by the spectral leakage of the RR harmonics, so there were more frequency mixing products in the low frequency range than in the high frequency.

For the high BP (hypertensive) rat of FIG. 16C, the radar-measured RR was 1.213 Hz and the calculated $m_r$ was 0.991 mm. In FIG. 16C, the HR peak cannot be identified from the original unfiltered spectrum (top plot). After filtering, the HR appeared at 3.638 Hz, which was exactly covered by the 3rd harmonic of the RR, and the frequency mixing products in high frequency spectrum can be seen.

Figure 17A:
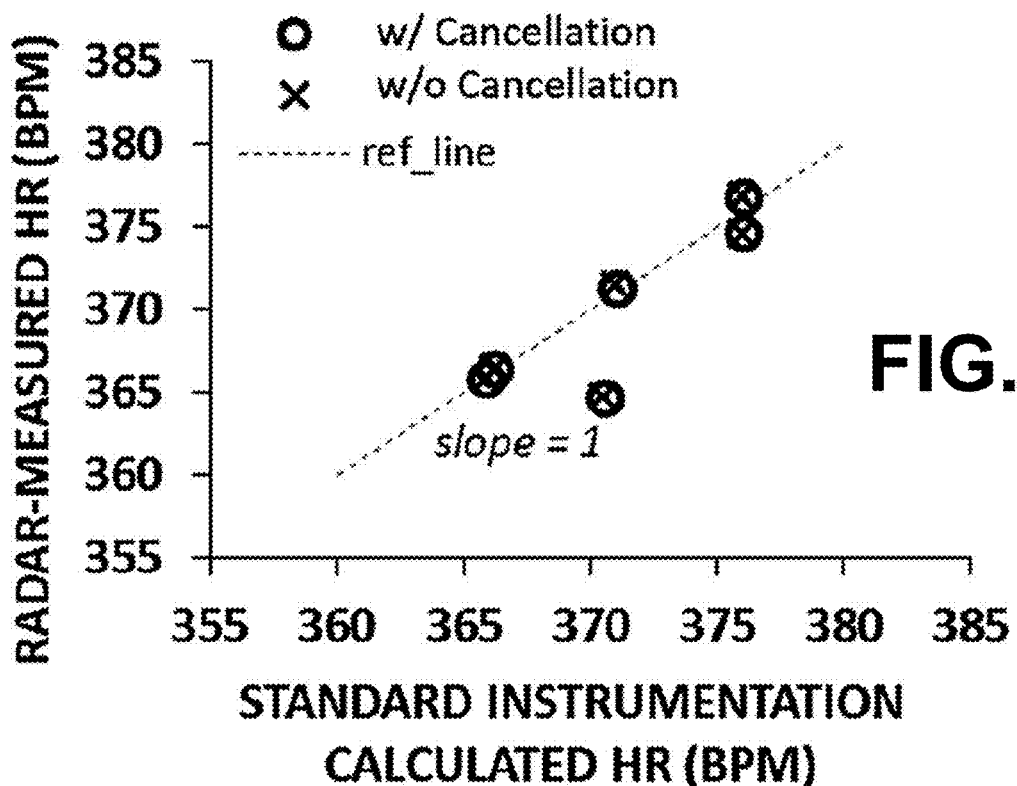
FIGS. 17A-17C are examples of correlation diagrams illustrating instrumentation calculated HR and radar-measured HR with and without applying the HCNDF, in accordance with various embodiments of the present disclosure.
Figure 17B:
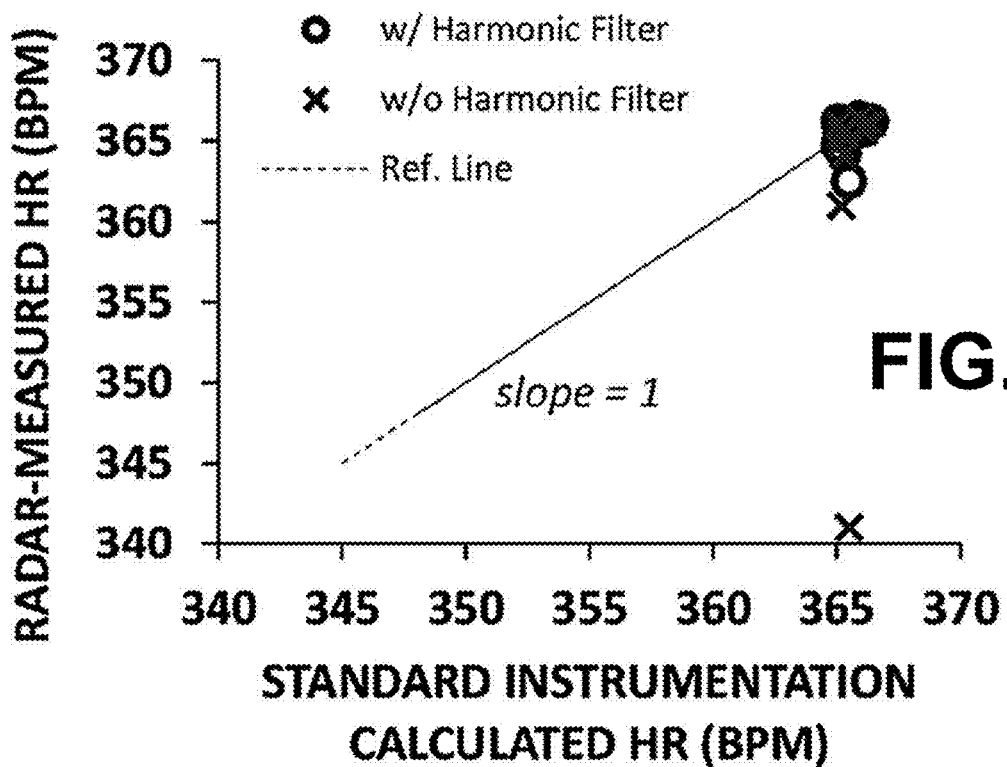
Figure 17C:
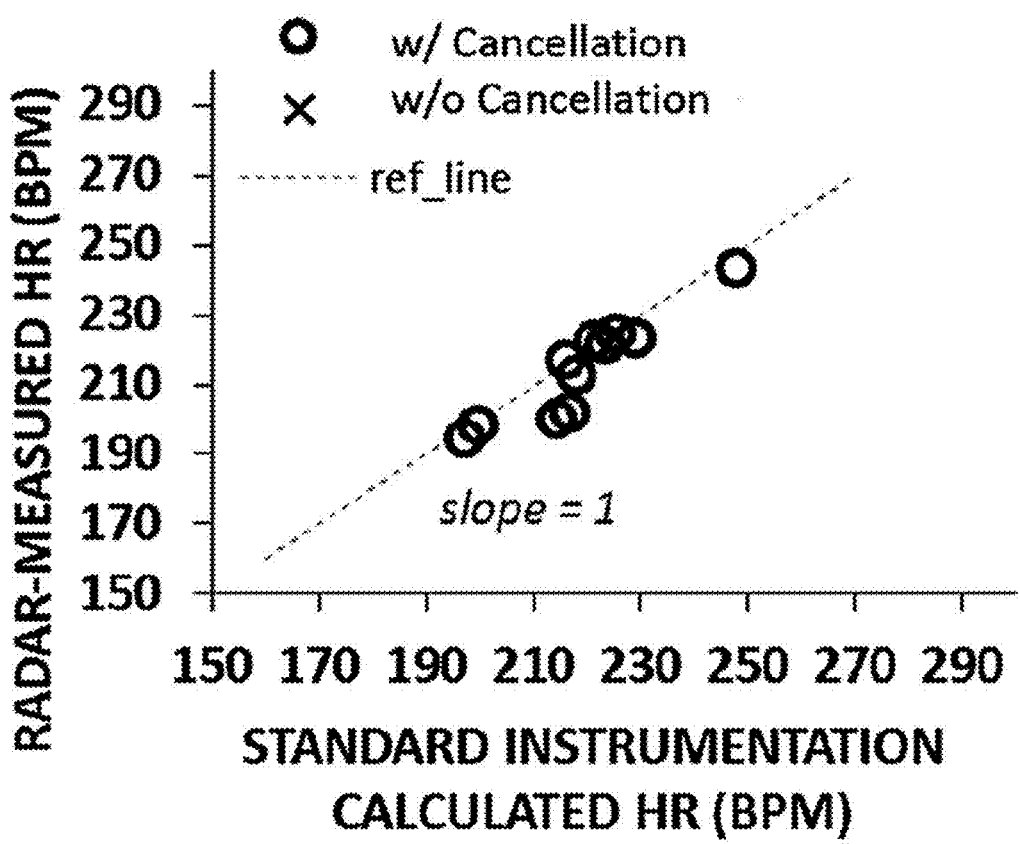

FIGS. 17A, 17B and 17C are correlation diagrams illustrating instrumentation calculated HR and radar-measured HR with and without applying the HCNDF. The plots are based on measurements of the conscious rat, the anesthetized rat and the drug-induced hypertensive rat, respectively. As shown in the correlation diagrams, the circles indicate radar measurements with HCNDF filtering and the crosses indicate radar measurements without HCNDF filtering. In FIG. 17A, the average error of HR detection is 0.39% with or without cancellation. The average error of the HR measurement in FIG. 17B was reduced from 0.82% to 0.19% after applying the filter. The error of the HR detection was further reduced from 90% to 1.8% in FIG. 17C, which is the overlapped case. Most importantly, the method corrected the radar-measured HR that had a large error due to the strong interference from the respiration harmonics.

Figure 18:
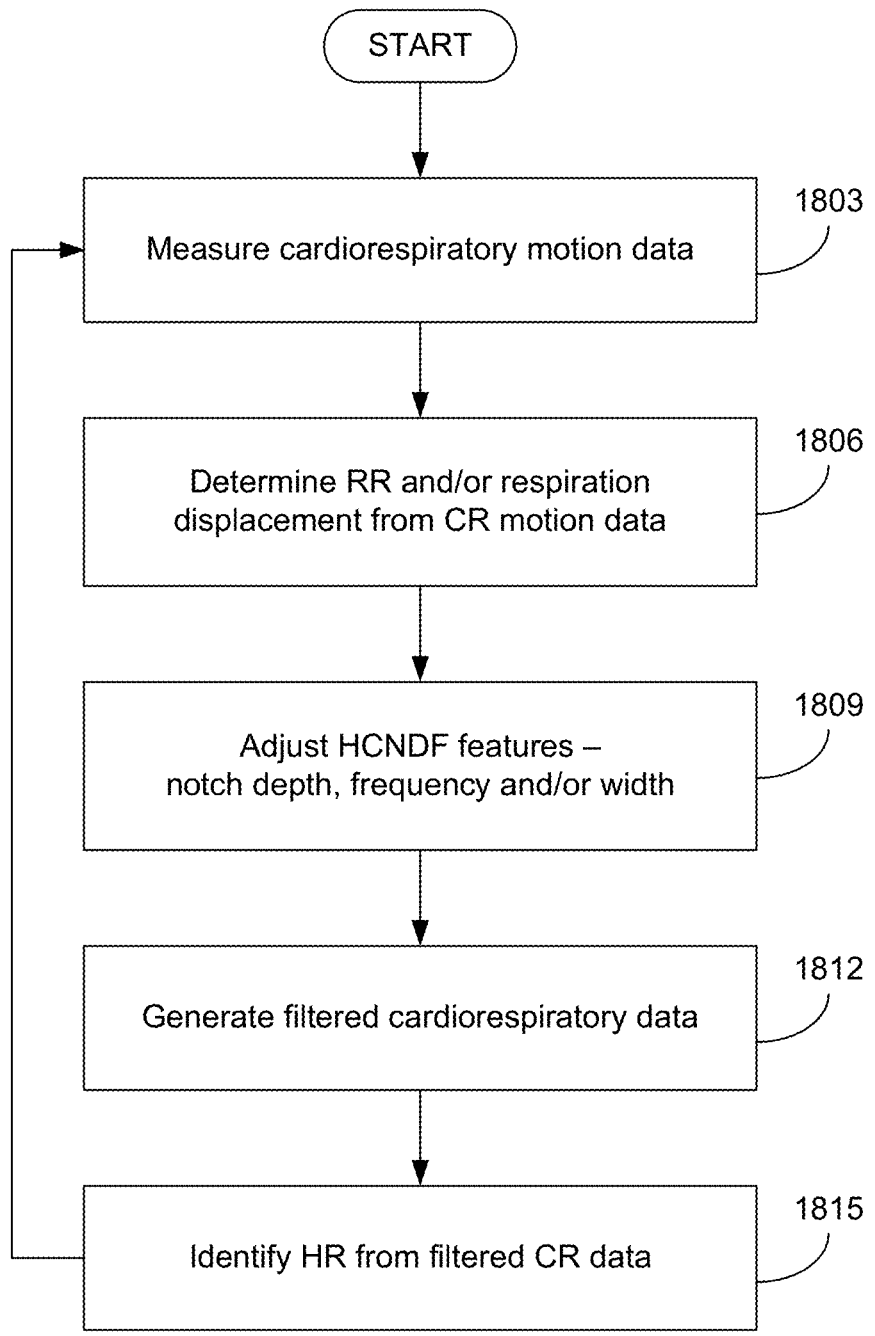
FIG. 18 is a flow chart illustrating an example of the operation of the adaptive HCNDF, in accordance with various embodiments of the present disclosure.

Referring next to FIG. 18, shown is a flow chart illustrating an example of cardiorespiratory evaluation using the HCNDF. Beginning with 1803, cardiorespiratory motion data is measured by a radar unit. For example, a 60 GHz radar can be used to measure cardiorespiratory motion of animals (e.g., laboratory rats) for determination of the HR. At 1809, the RR and/or the respiration displacement can be determined from the cardiorespiratory motion data. For example, the radar-measured cardiorespiratory data can be used to determine respiration displacement. The determination can be based upon the respiration fundamental frequency and/or respiration demodulation-generated (DG) harmonics identified from the radar-measured cardiorespiratory data. In addition, the RR can be identified from the fundamental frequency and/or harmonics of the fundamental frequency.

Features of the HCNDF can then be adjusted at 1809, based upon the respiration displacement and/or RR. Features that can be adjusted can include notch depth, notch frequency, and notch width. One or more of the features can be adjusted based upon the determined displacement and/or RR. The notch frequencies are based on the respiration fundamental frequency and its harmonics. For example, the HCNDF can include notches that correspond to the fundamental frequency ($f_r$), the second harmonic ($2f_r$), the third harmonic ($3f_r$), the fourth harmonic ($4f_r$), and the fifth harmonic ($5f_r$), as shown in FIG. 13A, or some other combination of fundamental and harmonics. As the RR frequency changes, the notch frequencies can be adjusted accordingly.

Notch depths can also be adjusted based upon amplitudes of the respiration fundamental frequency and the respiration DG harmonics. For example, the notch depths can be based upon one or more ratios of the respiration fundamental frequency and the respiration DG harmonics. In some implementations, the notch depth at the fundamental frequency can be based upon the respiration amplitudes, and the notch depths at the harmonic frequencies can be based upon a defined relationship with the notch depth at the fundamental frequency. The notch widths can also be adjusted. The widths can be based on the time window used to obtain the cardiorespiratory motion data. As the time window changes, the spectral resolution changes. As the time window increases, the notch width can be decreased. As the time window decreases, the notch width can be increased. For example, the notch widths can have a defined relationship with the length of the time window. As the time window changes, the notch widths can be changed in response to the change in the length of the time window.

At 1812, the cardiorespiratory motion data can be filtered using the HCNDF to generate filtered cardiorespiratory data, which can be used to identify the HR of the subject. The filtering can facilitate identification of a HR that falls on or near one of the respiration harmonics. As indicated, the flow chart can return to 1803 to repeat the process. In this way, the HCNDF can adaptively adjust to changing conditions of the subject. The evaluation to determine the HR can be carried out by a computing device that receives the cardiorespiratory motion data from the radar, or can be implemented by processing circuitry in the radar itself.

Figure 19:
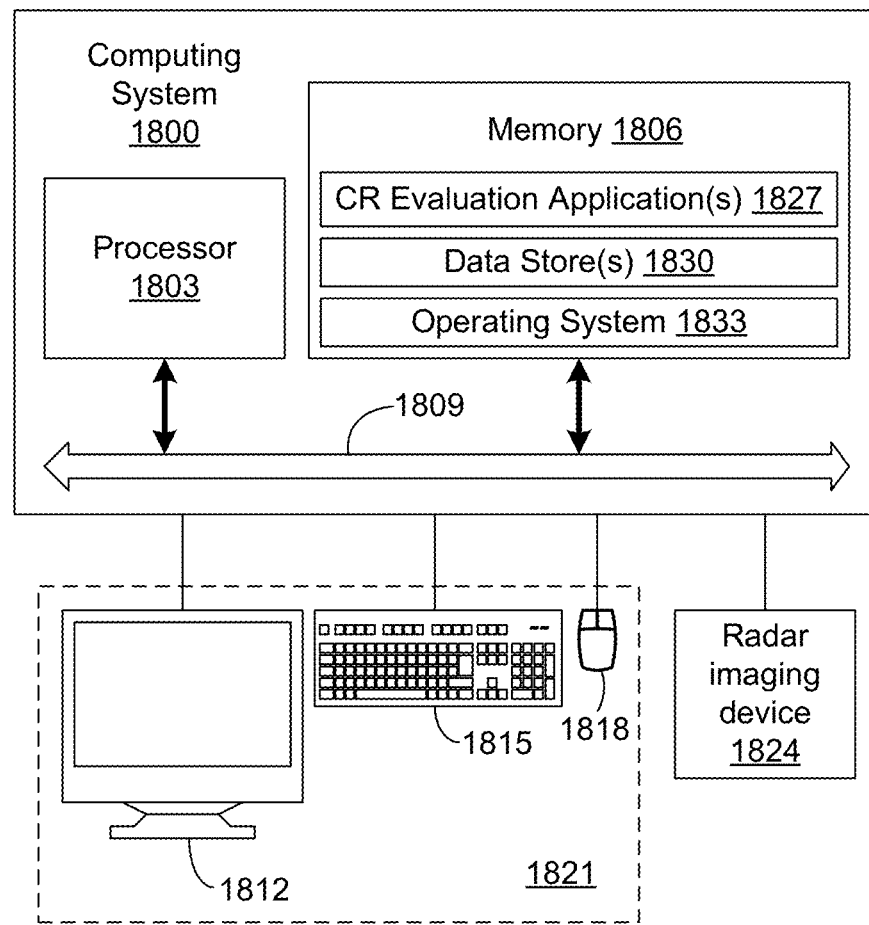
FIG. 19 is a schematic block diagram of a computing system, in accordance with various embodiments of the present disclosure.

With reference to FIG. 19, shown is a schematic block diagram of a computing system 1900 in accordance with various embodiments of the present disclosure. The computing system 1900 includes at least one processor circuit, for example, having a processor 1903 and a memory 1906, both of which are coupled to a local interface 1909. To this end, the computing system 1900 may comprise, for example, at least one computer, tablet, smart phone, or like computing device. The local interface 1909 may comprise, for example, a data bus with an accompanying address/control bus or other bus structure as can be appreciated. In addition, the computing system 1900 includes operator interface devices such as, e.g., a display device 1912, a keyboard 1915, and/or a mouse 1918. In some implementations, the operator interface device may be interactive display 1921 (e.g., a touch screen) that provides various functionality for operator interaction with the computing system 1900. Various imaging systems such as, e.g., radar imaging device 1924 may also interface with the computing system 1900 to allow for acquisition of signal measurements from a subject. In some implementations, the radar imaging device 1924 may interface with the computing system 1900 via a data acquisition board (DAQ) or other interfacing device. In some embodiments, the radar imaging device 1924 may be an array of detectors configured to be positioned about the monitored object or volume.

Stored in the memory 1906 are both data and several components that are executable by the processor 1903. In particular, stored in the memory 1906 and executable by the processor 1903 are various application modules or programs such as, e.g., a cardiorespiratory module, application, or program 1927 for evaluation of signal measurements from the radar imaging device 1924 using an adaptive harmonics comb notch digital filter (HCNDF), and/or other applications. Also stored in the memory 1906 may be a data store 1930 and other data. In addition, an operating system 1933 may be stored in the memory 1906 and executable by the processor 1903.

It is understood that there may be other applications that are stored in the memory 1906 and are executable by the processor 1903 as can be appreciated. Where any component discussed herein is implemented in the form of software, any one of a number of programming languages may be employed such as, for example, C, C++, C #, Objective C, Java®, JavaScript®, Perl, PHP, Visual Basic®, Python®, Ruby, Delphi®, Flash®, or other programming languages.

A number of software components are stored in the memory 1906 and are executable by the processor 1903. In this respect, the term "executable" means a program file that is in a form that can ultimately be run by the processor 1903. Examples of executable programs may be, for example, a compiled program that can be translated into machine code in a format that can be loaded into a random access portion of the memory 1906 and run by the processor 1903, source code that may be expressed in proper format such as object code that is capable of being loaded into a random access portion of the memory 1906 and executed by the processor 1903, or source code that may be interpreted by another executable program to generate instructions in a random access portion of the memory 1906 to be executed by the processor 1903, etc. An executable program may be stored in any portion or component of the memory 1906 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 1906 is defined herein as including both volatile and nonvolatile memory and data storage components. Volatile components are those that do not retain data values upon loss of power. Nonvolatile components are those that retain data upon a loss of power. Thus, the memory 1906 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 1903 may represent multiple processors 1903 and the memory 1906 may represent multiple memories 1906 that operate in parallel processing circuits, respectively. In such a case, the local interface 1909 may be an appropriate network that facilitates communication between any two of the multiple processors 1903, between any processor 1903 and any of the memories 1906, or between any two of the memories 1906, etc. The processor 1903 may be of electrical or of some other available construction.

Although the cardiorespiratory (or cardiorespiratory evaluation) module, application, or program 1927 and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flow chart of FIG. 18 shows a specific order of execution, it is understood that the order of execution may differ from that which is depicted. For example, the order of execution of two or more blocks may be scrambled relative to the order shown. Also, two or more blocks shown in succession in FIG. 18 may be executed concurrently or with partial concurrence. Further, in some embodiments, one or more of the blocks shown in FIG. 18 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the cardiorespiratory module, application, or program 1927 and/or application(s), that comprises software or code can be embodied in any non-transitory computer-readable medium for use by or in connection with an instruction execution system such as, for example, a processor 1903 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

In this disclosure, cardiorespiratory movement was analyzed and a guideline of implementing the displacement acquisition method was provided. Two groups of DG harmonics shown on the detected baseband spectrum were analyzed, and then used to identify the unknown HR. The selected DG harmonic ratios were examined through four vibration patterns: sinusoidal vibration, vibration containing the 2nd VG harmonic, vibration containing the 3rd VG harmonic, and vibration containing the 2nd & 3rd VG harmonics. Simulation results showed that the ratio of the 1st and the 2nd harmonics was the most reliable ratio to calculate the respiration displacement. Experiments were performed using anesthetized rats. The function of simultaneously measuring both displacements and frequencies of the cardiorespiratory movements (both respiration and heartbeat) using a 60 GHz radar was verified.

An adaptive HCNDF for removing respiration harmonics due to nonlinear Doppler phase demodulation effects was implemented. The experimental results demonstrated that the filter can be useful for HR measurement in a laboratory rat, which not only reduces the average error when the heartbeat is overwhelmed by respiratory movement, but also helps to identify the HR when it completely overlaps with the RR harmonics.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A method for heart rate measurement, comprising:
    determining, with a computing device, a respiratory rate (RR) and respiration displacement from radar-measured cardiorespiratory motion data;
    adjusting, with the computing device, notch depths of a harmonics comb notch digital filter (HCNDF) based upon the respiration displacement, wherein the respiration displacement is determined from a respiration fundamental frequency and respiration demodulation-generated (DG) harmonics identified from the radar-measured cardiorespiratory motion data;
    generating, with the computing device, filtered cardiorespiratory data by filtering the radar-measured cardiorespiratory motion data with the HCNDF; and
    identifying a heart rate (HR) from the filtered cardiorespiratory data.

2. The method of claim 1, wherein the notch depths are based upon amplitudes of the respiration fundamental frequency and the respiration DG harmonics.

3. The method of claim 1, wherein the notch depths are based upon one or more ratios of the respiration fundamental frequency and the respiration DG harmonics.

4. The method of claim 1, comprising adjusting notch frequencies of the HCNDF based upon the RR.

5. The method of claim 4, wherein the notch frequencies of the HCNDF correspond to a fundamental frequency of the RR and harmonics of the fundamental frequency.

6. The method of claim 5, wherein the HCNDF comprises notches corresponding to the fundamental frequency of the RR, a second harmonic frequency, and a third harmonic frequency.

7. The method of claim 6, wherein the HCNDF further comprises notches corresponding to a fourth harmonic frequency and a fifth harmonic frequency.

8. A method for heart rate measurement, comprising:
    determining, with a computing device, a respiratory rate (RR) and respiration displacement from radar-measured cardiorespiratory motion data;
    adjusting, with the computing device, notch depths of a harmonics comb notch digital filter (HCNDF) based upon the respiration displacement, wherein notch widths of the HCNDF are based upon a length of a time window over which the radar-measured cardiorespiratory motion data was obtained;
    generating, with the computing device, filtered cardiorespiratory data by filtering the radar-measured cardiorespiratory motion data with the HCNDF; and
    identifying a heart rate (HR) from the filtered cardiorespiratory data.

9. The method of claim 8, comprising adjusting the notch widths of the HCNDF in response to a change in the length of the time window.

10. The method of claim 9, wherein the notch widths are reduced in response to an increase in the length of the time window.

11. The method of claim 8, comprising adjusting notch frequencies of the HCNDF based upon the RR.

12. The method of claim 11, wherein the notch frequencies of the HCNDF correspond to a fundamental frequency of the RR and harmonics of the fundamental frequency.

13. A system, comprising:
    radar circuitry configured to transmit a single-tone carrier signal and receive a cardiorespiratory motion signal reflected from a monitored subject; and
    signal processing circuitry configured to:
        determine a respiration displacement from cardiorespiratory motion data based upon the cardiorespiratory motion signal;
        adjust notch depths of a harmonics comb notch digital filter (HCNDF) based upon the respiration displacement;
        generate filtered cardiorespiratory data by filtering the cardiorespiratory motion data with the HCNDF; and
        identify a heart rate (HR) from the filtered cardiorespiratory data,
    wherein the signal processing circuitry comprises data acquisition circuitry configured to sample quadrature signals of the cardiorespiratory motion signal and a processor configured to determine the respiration displacement and identify the HR based upon the sampled quadrature signals.

14. The system of claim 13, wherein the radar circuitry comprises a Doppler radar transceiver coupled to transmit and receive antennas.

15. The system of claim 13, wherein the respiration displacement is determined from a respiration fundamental frequency and respiration demodulation-generated (DG) harmonics identified from the cardiorespiratory motion data.

16. The system of claim 15, wherein the notch depths are based upon amplitudes of the respiration fundamental frequency and the respiration DG harmonics.

17. The system of claim 15, wherein the notch depths are based upon one or more ratios of the respiration fundamental frequency and the respiration DG harmonics.

18. A system, comprising:
radar circuitry configured to transmit a single-tone carrier signal and receive a cardiorespiratory motion signal reflected from a monitored subject; and
signal processing circuitry configured to:
- determine a respiration displacement from cardiorespiratory motion data based upon the cardiorespiratory motion signal;
- adjust notch depths of a harmonics comb notch digital filter (HCNDF) based upon the respiration displacement, wherein notch widths of the HCNDF are based upon a length of a time window over which the cardiorespiratory motion data was determined;
- generate filtered cardiorespiratory data by filtering the cardiorespiratory motion data with the HCNDF; and
- identify a heart rate (HR) from the filtered cardiorespiratory data.

19. The system of claim 18, wherein the signal processing circuitry is further configured to adjust notch frequencies of the HCNDF based upon a respiratory rate (RR) determined from the cardiorespiratory motion data.

20. The system of claim 19, wherein the notch frequencies of the HCNDF correspond to a fundamental frequency of the RR and harmonics of the fundamental frequency.

21. The system of claim 18, wherein the signal processing circuitry is further configured to adjust the notch widths of the HCNDF in response to a change in the length of the time window.

* * * * *

UNITED STATES PATENT AND TRADEMARK OFFICE
CERTIFICATE OF CORRECTION

| | |
|---|---|
| PATENT NO. | : 11,944,462 B2 |
| APPLICATION NO. | : 17/462665 |
| DATED | : April 2, 2024 |
| INVENTOR(S) | : Jenshan Lin, Linda Frances Hayward and Tien-Yu Haung |

It is certified that error appears in the above-identified patent and that said Letters Patent is hereby corrected as shown below:

On the Title Page

Item (72) Inventors should read: Jenshan Lin, Linda Frances Hayward, and Tien-Yu Huang Signed and Sealed this
Twelfth Day of November, 2024

Katherine Kelly Vidal
*Director of the United States Patent and Trademark Office*